United States Patent [19]

Wickstrom et al.

[11] Patent Number: 5,703,223
[45] Date of Patent: Dec. 30, 1997

[54] SOLID PHASE SYNTHESIS OF OLIGONUCLEOTIDES WITH STEREOSPECIFIC SUBSTITUTED PHOSPHONATE LINKAGES BY PENTAVALENT GRIGNARD COUPLING

[75] Inventors: Eric Wickstrom; Christine Le Bec, both of Philadelphia, Pa.

[73] Assignee: Thomas Jefferson University, Philadelphia, Pa.

[21] Appl. No.: 300,259

[22] Filed: Sep. 2, 1994

[51] Int. Cl.$^6$ .................. C07H 1/00; C07H 21/04
[52] U.S. Cl. .................. 536/25.33; 536/25.3
[58] Field of Search .................. 536/25.33, 25.3

[56] References Cited

U.S. PATENT DOCUMENTS

| | | | |
|---|---|---|---|
| 4,415,732 | 11/1983 | Caruthers et al. | 536/25.3 |
| 5,212,295 | 5/1993 | Cook | 536/26.7 |
| 5,386,023 | 1/1995 | Sanghvi et al. | 536/25.3 |
| 5,420,328 | 5/1995 | Campbell | 558/110 |

FOREIGN PATENT DOCUMENTS

| | | |
|---|---|---|
| WO94/00473 | 1/1994 | WIPO . |
| WO94/00472 | 1/1994 | WIPO . |

OTHER PUBLICATIONS

The 1992 Sigma Chemical Catalog, Sigma Chemical Company, p. 1732.

Stec, et al., "Stereospecific Synthesis of P–Chiral Analogs of Oligonucleotides", Chapter 14 in *Methods in Molecular Biology, vol. 20: Protocols for Oligonucleotides and Analogs*, S. Agrawal (ed.), Humana Press, Totowa, NJ (1993).

Lesnikowski, et al., *Nucleic Acids Research*, 16: 11625–11689 (1988).

Bonora, et al., *Nucleic Acids Research*, 21: 1213–1217 (1993).

Applied Biosystems, *Research News*, Model 390Z, Feb. 1994.

*Primary Examiner*—Gary L. Kunz
*Attorney, Agent, or Firm*—Seidel, Gonda, Lavorgna & Monaco, PC

[57] ABSTRACT

The present invention provides a method for producing an oligonucleotide having stereospecific substituted phosphonate linkages by use of a pentavalent Grignard coupling reaction on a solid phase support. The method can be used for automated synthesis of oligonucleotides having sequential equatorial or axial stereospecific substituted phosphonate linkages.

19 Claims, No Drawings

SOLID PHASE SYNTHESIS OF OLIGONUCLEOTIDES WITH STEREOSPECIFIC SUBSTITUTED PHOSPHONATE LINKAGES BY PENTAVALENT GRIGNARD COUPLING

REFERENCE TO GOVERNMENT GRANT

The invention described herein was made, in part, in the course of work supported by United States Public Health Service grant CA-60139 awarded by the National Institutes of Health.

FIELD OF THE INVENTION

The present invention relates to the synthesis of oligonucleotides with stereospecific substituted phosphonate linkages.

BACKGROUND OF THE INVENTION

Oligonucleotides have been employed diversely in utilities ranging from diagnosis and therapy of disease to discovery, cloning and synthesis of nucleic acids. For example, oligonucleotides can be used as probes to identify target nucleic acids that are present in vivo, in tissue samples or that are immobilized onto a filter or membrane. After identification by the oligonucleotide, a target nucleic acid can be cloned and an oligonucleotide can be used to prime the synthesis of that nucleic acid. Hybridization patterns of an oligonucleotide to a nucleic acid that differ from normal hybridization patterns are frequently useful in diagnosis of disease. Moreover, there has been great interest recently in developing oligonucleotides as therapeutic agents which can regulate the biological function of cellular or viral nucleic acids.

Interest in oligonucleotides as therapeutic agents has arisen from observations of naturally occurring complementary, or antisense, RNA used by some cells to control protein expression. More recently, synthetic oligonucleotides have been used with success to inhibit gene expression. For example, oligonucleotides were initially utilized to inhibit replication of Rous sarcoma virus, Zamecnik et al., *Proc. Natl. Acad. Sci. USA* 75:280–284 (1978).

Since such initial studies, a variety of oligonucleotides have been used to control many different genes in cell culture derived from diverse organisms, including viruses, bacteria and plants, and, a few in whole organisms, such as mice. See, for example, Wickstrom et al., *Cancer Res.* 52: 6741–6745 (1992); Ratajcak et al., *Proc. Natl. Acad. Sci. USA*, 89: 11823–11827 (1992); and Gray et al., *Cancer Res.* 53:577–580 (1993).

However, the development of oligonucleotides for in vivo regulation of biological processes has been hampered by several long-standing problems, including nuclease sensitivity, lack of specificity of binding to target nucleic acids, and poor cell penetrability. Attempts to synthesize derivatives which counteract these problems have led to derivatives with substitutions in the normal phosphodiester linkage (—O—PO$_2$—O—), such as phosphorothioates, Stec et al., *J. Amer. Chem. Soc.* 106: 6077–6079 (1984), borane phosphonates, Sood et al., *J. Amer. Chem. Soc.* 112:9000–9001 (1990), and those which replace ionic moieties, in order to allow the DNA to diffuse through the cellular membranes, such as methylphosphonates, Miller, P. S., "Non-ionic antisense oligonucleotides", Chapter 4, in *Oligodeoxynucleotides: Antisense Inhibitors of Gene Expression*, Cohen, J. S. (ed.), CRC Press, Boca Raton, Fla., 79–95 (1989). Moreover, uncharged oligodeoxynucleoside methylphosphonates have been shown to overcome these problems in that they are resistant to nucleases, they are readily taken up by cells and specifically inhibit expression of oncogenes or viral genes. Chang, et al., *Prospects for Antisense Nucleic Acid Therapeutics for Cancer and AIDS*, Wickstrom, E. (ed.), Wiley-Liss, New York, 115–124 (1991).

However, the substitution of either of the two nonbridging oxygens within the normal phosphodiester bond generates a chiral phosphate which can exist in two stereoconfigurations, namely equatorial and axial. The relatively high concentrations of substituted oligonucleotides required to achieve a significant therapeutic effect is apparently due to inefficient binding by oligonucleotides which contain substituted phosphonate linkages in the axial stereoconfiguration, Miller et al., *Biotechnology* 9: 358–362 (1991).

Current synthetic procedures, using a trivalent coupling of the phosphonate linkage, are non-stereo-specific and typically generate a linkage having either stereoconfiguration as each nucleotide is added. The resulting oligonucleotide thus has a mixture of equatorial and axial linkages. However, racemic methylphosphonate oligomers show limited potency as antisense inhibitors of gene expression, Wickstrom, E., *Trends in Biotechnology* 10: 281–287 (1992). In addition, the physical characteristics of the equatorial and axial isomers differ significantly, with the equatorial form having higher melting temperatures, Vyazovkina et al., *Nucleic Acids Res.* 22: 2404–2409 (1994), and the ability to bind much more strongly than the axial isomer to complementary sequences, Miller et al., *J. Biol. Chem.* 235: 9659–9665 (1980); and Lesnikowski et al., *Nucleic Acids Res.* 18: 2109–2115 (1990). Therefore, it is likely that an oligonucleotide containing only equatorial nucleotides will display significantly greater potency as antisense or antigene therapeutics than do racemic oligomers. Hence, a procedure which efficiently and accurately produces nucleotides with stereospecific substituted phosphonate linkages and one which could be automated would present an improvement over available procedures.

Prior methods for obtaining oligonucleotides with stereospecific substituted phosphonate linkages have been performed in solution, which require steps that are not readily adapted to automation. In solution synthesis, it is necessary to purify the product isomers after addition of each nucleotide, which results in decreasing yields after each addition. Thus, solution methods are generally used only for obtaining very short oligonucleotides, i.e., oligonucleotides having up to eight nucleotides. For example, Lesnikowski et al., *Nucleic Acids Res.* 16: 11675–11689 (1988) and Stec et al., "Stereospecific Synthesis of P-Chiral Analogs of Oligonucleotides", Chapter 14, in *Methods in Molecular Biology*, Vol. 20: *Protocols for Oligonucleotides and Analogs*, Agrawal, S. (ed.), Humana Press, Totawa, N.J., 285–313 (1993), have reported the synthesis of stereospecific dimer, trimer and tetramer oligonucleotides using Grignard reagent activation of the 5'—OH group nucleotide. Lesnikowski et al., *Nucleic Acids Res.* 18: 2109–2115 (1990) have reported synthesis of an octamer (dT) with a central racemic methylphosphonate linkage, and Vyazovkina et al., *Nucleic Acids Res.* 22: 2404–2409 (1994) report the synthesis of a heptamer with stereospecific linkages. However, to date there has been no disclosure of a solid phase method which permits efficient automated synthesis of a stereospecific substituted phosphonate linkages.

ABBREVIATIONS AND DEFINITIONS

It is customary for those skilled in the art to use abbreviations for reagents used to make oligonucleotides in a manner well-known to the art. These customary abbreviations are set forth herein below and may be utilized in the text of this specification.

In addition, this invention has adopted certain terms or conventions to describe the invention. A summary of these definitions follows the abbreviations.

Abbreviations:
Ax: axial stereoconfiguration about a chiral center
bz: benzoyl
DCC: dicyclohexylcarbodiimide
DCE: 1,2-dichloroethane
DMAP: dimethylaminopyridine
DMT: dimethoxytrityl
DNA: deoxyribose nucleic acid
Eq: equatorial stereoconfiguration about a chiral center
HLP: high-loaded polystyrene support polyethyleneglycol (PEG) coated polystyrene
ibu: isobutyryl
npe: 2-(4-nitrophenyl)ethyl
npeoc: 2-(4-nitrophenyl)ethoxycarbonyl
PEG: polyethylene glycol
RNA ribose nucleic acid
tbds: (tert-butyl)dimethylsilyl
TCA: trichloroacetic acid
THF: tetrahydrofuran Definitions:

The term substituted phosphonate linkage as used herein means the normally occurring phosphodiester bond having the formula

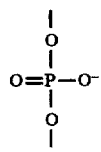

in which one of the non-bridging oxygens has been substituted with the group M to form the phosphonate linkage

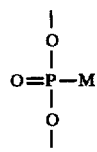

in which M is independently selected from the group consisting of lower alkyl, lower aryl, thio, lower thioalkyl, $BH_3$, $BF_3$, lower boranoalkyl, amino, aminoalkyl and dialkyl amino.

The term "solid support" means a solid particle, the surface of which contains a reactive chemical linker group capable of joining the support to either the 2' or 3' position of a pentose sugar moiety in a nucleoside.

The term "precipitable soluble polymer" means a polymer soluble in a particular solvent under a prescribed set of conditions, but which is capable of being precipitated out of the solution by substituting a different solvent and/or adjusting the solvent conditions.

SUMMARY OF THE INVENTION

The present invention relates to a method for producing an oligonucleotide having stereospecific substituted phosphonate linkages by use of a pentavalent Grignard coupling on a solid phase support. The use of a solid support allows the desired product to be readily separated from the reagent solvents without the use of a purification step after each nucleotide addition. This results in more efficient synthesis times and circumvents the prior problem of decreasing yield with the addition of each nucleotide.

Accordingly, the invention is a method for producing a dinucleotide having a stereospecific substituted phosphonate linkage between a first and a second nucleoside, wherein said dinucleotide has the formula of A or A':

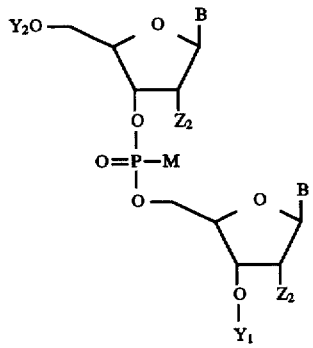

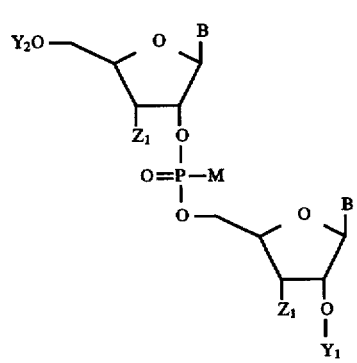

wherein:

$Y_1$ is a hydrogen or $V_1$;

$Y_2$ is a hydrogen or $V_2$; and

B is independently selected from the group consisting of substituted and unsubstituted purine and pyrimidine bases;

$Z_1$ and $Z_2$ are independently selected from the group consisting of hydrogen, hydroxyl, and $OY_3$ where $Y_3$ is substituted or unsubstituted alkyl; and M is selected from the group consisting of alkyl, aryl, thio, borano, and amino.

which method comprises:

(a) reacting a 5'-deprotected nucleoside having formula I or Ia:

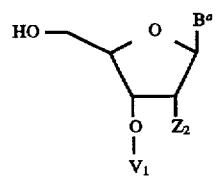

or

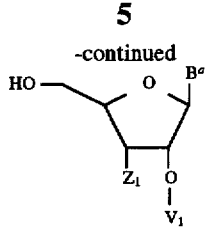

wherein:

$B^a$ is selected from the group of substituted and unsubstituted protected purine and protected pyrimidine bases;

$Z_1$ and $Z_2$ are selected from the group consisting of hydrogen, hydroxyl and $OY_3$, where $Y_3$ is substituted or unsubstituted alkyl, and $V_1$ is a solid support;

with a Grignard reagent of the formula, R—Mg—X, wherein:

R is a substituted or unsubstituted alkyl, allyl, aralkyl or aryl group; and

X is a halogen;

(b) coupling the product of (a) with a pure diastereoisomer of a 5'-protected nucleotide of formula II or IIa:

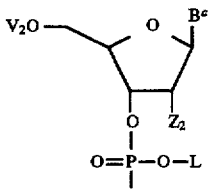

or

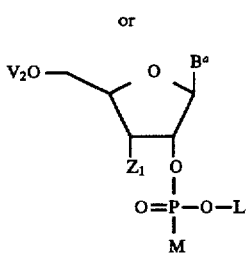

wherein:

$B^a$ is defined as above;

$V_2$ is a protecting group;

$Z_1$ and $Z_2$ are defined as above,

M is defined as above; and

L is a leaving group;

under anhydrous conditions sufficient to produce said stereospecific substituted phosphonate linkage; and (c) when $V_2$ is a protecting group, optionally removing the $V_2$ protecting group.

According to another embodiment, the invention is a method for producing an oligonucleotide with stereospecific substituted phosphonate linkages, wherein said oligonucleotide has the formula of Q or Q';

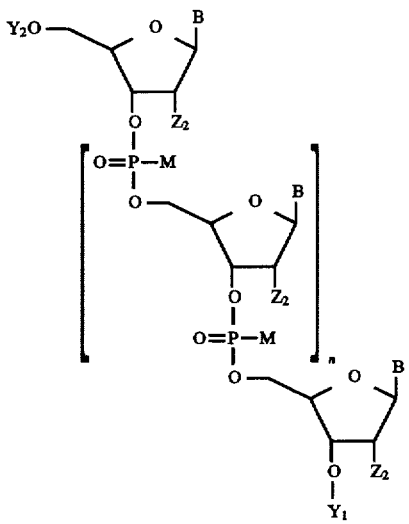

or

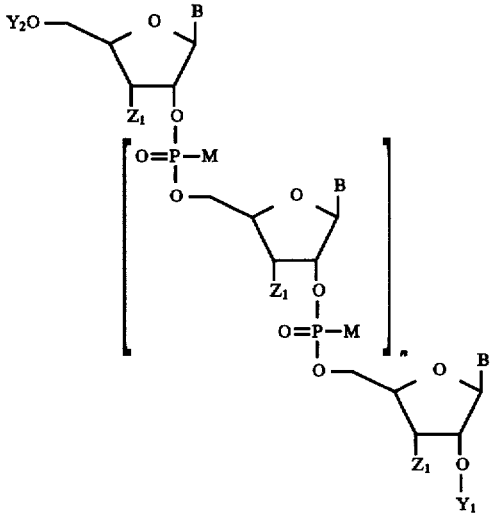

wherein:

$Y_1$ is a hydrogen or $V_1$; $Y_2$ is a hydrogen or $V_2$;

B is independently selected from the group consisting of substituted and unsubstituted purine and pyrimidine bases;

$Z_1$ and $Z_2$ are independently selected from the group consisting of hydrogen, hydroxyl and $OY_3$, where $Y_3$ is substituted and unsubstituted alkyl;

M is selected from the group consisting of alkyl, aryl, thio, borano and amino.

n is an integer from 0 to 200;

which method comprises:

(a) reacting a 5'-deprotected terminal nucleoside having formula I or Ia:

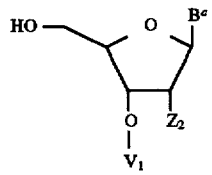

-continued or

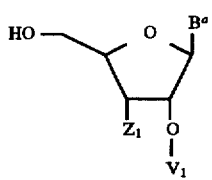

Ia wherein:

$B^a$ is selected from the group of substituted and unsubstituted protected purine and protected pyrimidine bases;

$Z_1$ and $Z_2$ are selected from the group consisting of hydrogen, hydroxyl and $OY_3$, where $Y_3$, is a substituted or unsubstituted alkyl, $V_1$ is a solid support;

with a Grignard reagent of the formula, R—Mg—X, where
R is a substituted or unsubstituted alkyl, allyl, aralkyl or aryl group; and
X is a halogen;

(b) coupling the product of (a) with a pure diastereoisomer of a 5'-protected nucleotide of formula II or IIa:

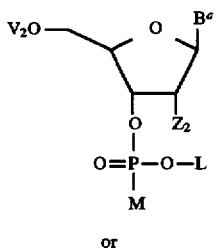

II or

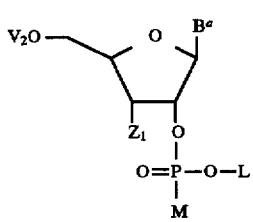

IIa wherein:
$B^a$ is defined as above;
$V_2$ is a protecting group;
$Z_1$ and $Z_2$ are defined as above;
M is defined as above; and
L is a leaving group;

under anhydrous conditions sufficient to produce a new 5'-protected terminal nucleotide with said stereospecific substituted phosphonate linkage;

(c) removing the $V_2$ protecting group from said new 5'-protected terminal nucleotide;

(d) reacting the product of (c) with a Grignard reagent of the formula R—Mg—X, defined as above;

(e) reacting the product of (d) with another pure diastereoisomer of a 5'-protected nucleotide according to Formula II or IIa under conditions sufficient to produce a stereospecific substituted phosphonate linkage and so generate a new 5'-protected terminal nucleotide;

(f) repeating steps (c) through (e) to extend said polynucleotide chain n−1 times; and (g) when $V_2$ is a protecting group, optionally removing the $V_2$ protecting group.

The invention described herein further embodies a method for producing a dinucleotide having a stereospecific substituted phosphonate linkage between a first and a second nucleoside, wherein said dinucleotide has the formula of A or A':

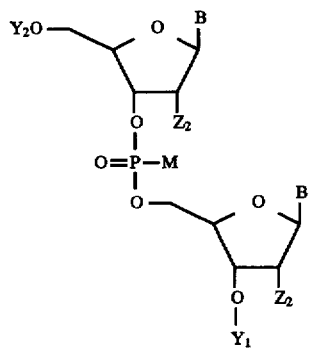

A or

A' wherein:
$Y_1$ is a hydrogen or $V_1$;
$Y_2$ is a hydrogen or $V_2$; and
B is independently selected from the group consisting of substituted and unsubstituted purine and pyrimidine bases;
$Z_1$ and $Z_2$ are independently selected from the group consisting of hydrogen, hydroxyl, and $OY_3$ where $Y_3$ is substituted or unsubstituted alkyl; and
M is selected from the group consisting of alkyl, aryl, thio, borano and amino.

which method comprises:

(a) reacting a 5'-deprotected nucleoside having formula I or Ia:

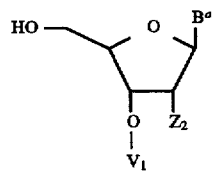

I or

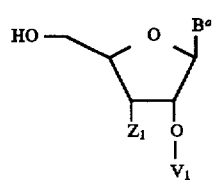

Ia wherein:

9

$B^a$ is selected from the group of substituted and unsubstituted protected purine and protected pyrimidine bases;

$Z_1$ and $Z_2$ are selected from the group consisting of hydrogen, hydroxyl, and $OY_3$, where $Y_3$ is a substituted or unsubstituted alkyl; and $V_1$ is a precipitable soluble polymer;

with a Grignard reagent of the formula, R—Mg—X, where

R is a substituted or unsubstituted alkyl, allyl, aralkyl or aryl group; and

X is a halogen;

(b) coupling the product of (a) with a pure diastereoisomer of a 5'-protected nucleotide of formula II or IIa:

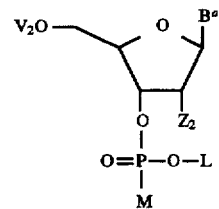
II or

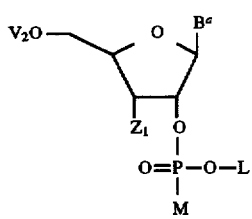
IIa wherein:

$B^a$ is defined as above;

$V_2$ is a protecting group;

$Z_1$ and $Z_2$ are defined as above;

M is defined as above; and

L is a leaving group;

under anhydrous conditions sufficient to produce said stereospecific substituted phosphonate linkage;

(c) precipitating the product of (b) to remove the dinucleotide with said stereospecific substituted phosphonate linkage from solution; and (d) when $V_2$ is a protecting group, optionally removing the $V_2$ protecting group.

The invention described herein also contemplates another embodiment which is a method for producing of an oligonucleotide with stereospecific substituted phosphonate linkages, wherein said oligonucleotide has the formula of Q or Q':

10

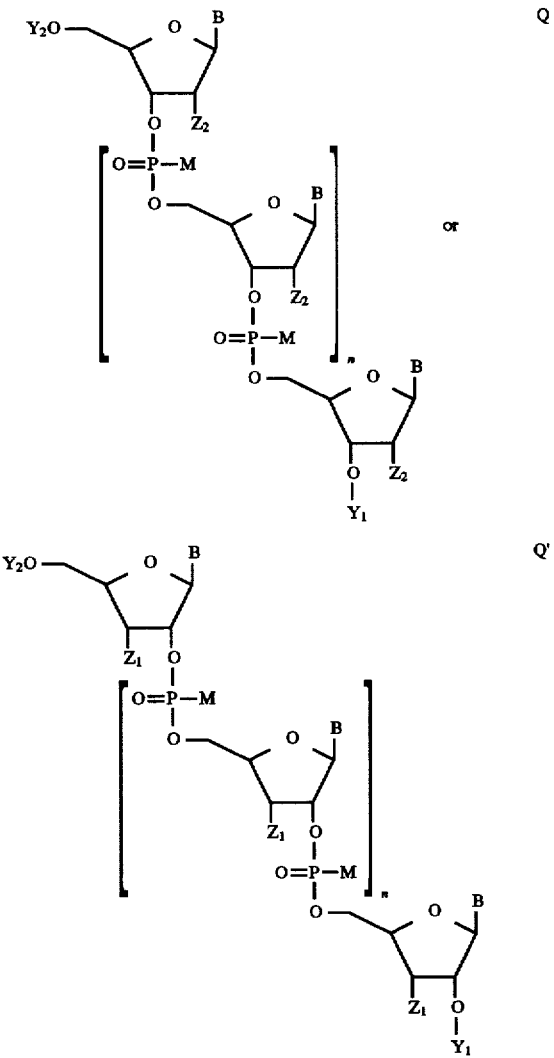

wherein:

$Y_1$ is a hydrogen or $V_1$;
$Y_2$ is a hydrogen or $V_2$; and
B is independently selected from the group consisting of substituted and unsubstituted purine and pyrimidine bases;

$Z_1$ and $Z_2$ are independently selected from the group consisting of hydrogen, hydroxyl and $OY_3$, where $Y_3$ is substituted and unsubstituted alkyl;

M is selected from the group consisting of alkyl, aryl, thio, borano and amino.

n is an integer from 0 to 200;

which method comprises:

(a) reacting a 5'-deprotected terminal nucleoside having the formula I or Ia:

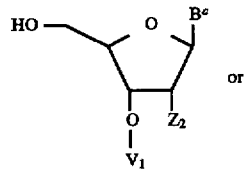
I or

-continued

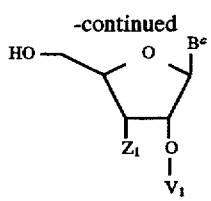

Ia wherein:

$B^a$ is selected from the group of substituted and unsubstituted protected purine and protected pyrimidine bases;

$Z_1$ and $Z_2$ are selected from the group consisting of hydrogen, hydroxyl and $OY_3$, where $Y_3$ is a substituted or unsubstituted alkyl; and $V_1$ is a precipitable soluble polymer;

with a Grignard reagent of the formula, R—Mg—X, where:

R is a substituted or unsubstituted alkyl, allyl, aralkyl or aryl group; and

X is a halogen;

(b) coupling the product of (a) with a pure diastereoisomer of a 5'-protected nucleotide of formula II or IIa:

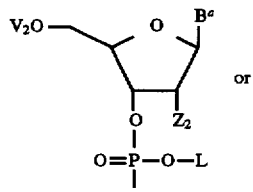

II

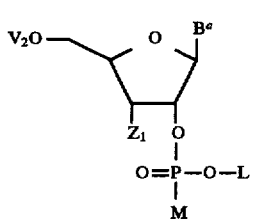

IIa wherein:

$B^a$ is defined as above;

$V_2$ is a protecting group;

$Z_1$ and $Z_2$ are defined as above;

M is defined as above; and

L is a leaving group;

under anhydrous conditions sufficient to produce a new 5'-protected terminal nucleotide with said stereospecific substituted phosphonate linkage;

(c) precipitating the product of (b) to remove the oligonucleotide with said stereospecific substituted phosphonate linkage from solution;

(d) dissolving the product of (c) in a solvent to return the product to solution to add another nucleotide with said stereospecific phosphonate linkage to said oligonucleotide formed in step (b);

(e) removing the $V_2$ protecting group from said new 5'-protected terminal nucleotide;

(f) reacting the product of (e) with a Grignard reagent of the formula R—Mg—X, defined as above;

(g) reacting the product of (f) with another pure diastereoisomer of a 5'-protected nucleotide according to Formula II or IIa under anhydrous conditions sufficient to produce a stereospecific substituted phosphonate linkage and so generate a new 5'-protected terminal nucleotide;

(h) repeating steps (b) through (g) to extend said polynucleotide chain n–1 times; and (i) when $V_2$ is a protecting group, optionally removing $V_2$ protecting group.

A still further embodiment of this invention includes a method for producing a Grignard-nucleoside intermediate on a support, which intermediate is of the formula III or IIIa:

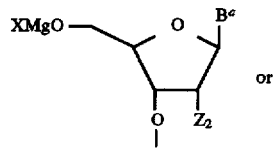

III

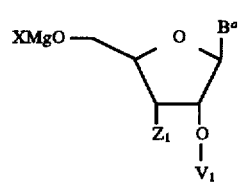

IIIa wherein:

$B^a$ is selected from the group consisting of substituted and unsubstituted protected purine and protected pyrimidine bases;

$Z_1$ and $Z_2$ are selected from the group of hydrogen, hydroxyl and $OY_3$, where $Y_3$ substituted and unsubstituted alkyl;

X is a halogen; and $V_1$ is selected from the group consisting of a solid support and a precipitable soluble polymer;

which method comprises:

reacting a 5'-deprotected nucleoside having formula I or Ia:

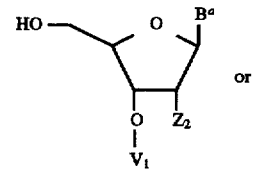

I

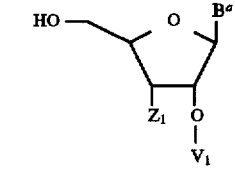

Ia wherein:

$B^a$ is defined as above;

$Z_1$ and $Z_2$ are defined as above; and $V_1$ is defined as above;

with a Grignard reagent of the formula, R—Mg—X, where

R is a substituted or unsubstituted alkyl, allyl, aralkyl, or aryl group; and

X is defined as above;

under anhydrous conditions sufficient to produce said Grignard-nucleoside intermediate.

According to yet another embodiment, the invention is a method for producing a dinucleotide having a stereospecific substituted phosphonate linkage between a first and a second nucleoside, which method comprises:
- (a) reacting a base protected nucleoside linked to a solid support through the 2' or 3' position of said nucleoside, with a compound of the formula R—Mg—X, where R is a substituted or unsubstituted alkyl, allyl, aralkyl or aryl, and X is a halogen;
- (b) coupling the product of (a) with a stereo-specific base protected nucleotide, having a substituted phosphoryl moiety of the formula

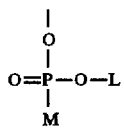

linked through the 2' or 3' position of said nucleotide, where M is selected from the group consisting of alkyl, aryl, thio, borano and amino, and L is a leaving group, under anhydrous conditions sufficient to link the base protected nucleoside of (a) to the substituted phosphoryl moiety of said nucleotide and generate said stereospecific substituted phosphonate linkage in a new 5'-terminal nucleotide; and
- (c) optionally removing the protecting group from the new 5'-terminal nucleotide.

The invention also includes an embodiment for a method for producing an oligonucleotide having stereospecific substituted phosphonate linkages, which method comprises:
- (a) reacting a 5'-deprotected base protected nucleoside linked to a solid support through the 2' or 3' position of said nucleoside, with a compound of the formula R—Mg—X, where R is a substituted or unsubstituted alkyl, allyl, aralkyl or aryl, and X is a halogen;
- (b) coupling the product of (a) with a stereo-specific base protected nucleotide, having a substituted phosphoryl moiety of the formula

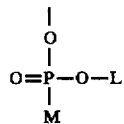

linked through the 2' or 3' position of said nucleotide, where M is selected from the group consisting of alkyl, aryl, thio, borano and amino, and L is a leaving group, under anhydrous conditions sufficient to link the base protected nucleoside of (a) to the substituted phosphoryl moiety of said nucleotide and generate said stereospecific phosphonate linkage in a new 5'-terminal nucleotide;
- (c) removing the protecting group from the new 5'-terminal nucleotide;
- (d) reacting the product of (c) with a compound of the formula R—Mg—X, defined as above; and
- (e) repeating steps (b) through (e) one or more times to extend said polynucleotide chain to the desired length.

The invention described herein also includes an embodiment for a method for producing a dinucleotide having a stereospecific substituted phosphonate linkage between a first and a second nucleoside, which method comprises:
- (a) reacting a 5'-deprotected base protected nucleoside linked to a precipitable soluble polymer through the 2' or 3' position of said nucleoside, with a compound of the formula R—Mg—X, where R is a substituted or unsubstituted alkyl, allyl, aralkyl or aryl, and X is a halogen;
- (b) coupling the product of (a) with a stereo-specific base protected nucleotide, having a substituted phosphoryl moiety of the formula

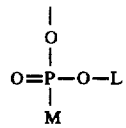

linked through the 2' or 3' position of said nucleotide, where M is selected from the group consisting of alkyl, aryl, thio, borano, amino, amino-alkyl and lower amino alkyl, and L is a leaving group under anhydrous conditions sufficient to link the base protected nucleoside of (a) to the substituted phosphoryl moiety of said nucleotide and generate said stereospecific phosphonate linkage in a new 5'-terminal nucleotide;
- (c) precipitating out the product of (b) from solution to remove said dinucleotide having a stereo-specific substituted phosphonate linkage; and
- (d) optionally removing the protecting group from the new 5'-terminal nucleotide.

According to still another embodiment, the invention is a method for producing an oligonucleotide having stereospecific substituted phosphonate linkages, which method comprises:
- (a) reacting a 5'-deprotected base protected nucleoside linked to a precipitable soluble polymer through the 2' or 3' position of said nucleoside, with a compound of the formula R—Mg—X, where R is a substituted or unsubstituted alkyl, allyl, aralkyl or aryl, and X is a halogen;
- (b) coupling the product of (a) with a stereo-specific base protected nucleotide, having a substituted phosphoryl moiety of the formula

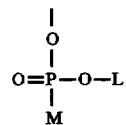

linked through the 2' or 3' position of said nucleotide, where M is selected from the group consisting of alkyl, aryl, thio, borano and amino, and L is a leaving group, under anhydrous conditions sufficient to link the base protected nucleoside of (a) to the substituted phosphoryl moiety of said nucleotide and generate said stereospecific phosphonate linkage in a new 5'-terminal nucleotide;
- (c) precipitating out the product of (b) from solution to remove said dinucleotide having a stereo-specific substituted phosphonate linkage;
- (d) reacting the product of (c) with a compound of the formula R—Mg—X, defined as above;
- (e) dissolving the product of (c) in a solvent to return the product to solution to generate a new oligonucleotide with said stereospecific substituted phosphonate linkage;
- (f) removing the protecting group from the new 5'-terminal nucleotide;
- (g) reacting the product of (f) with another stereospecific base protected nucleotide of the formula of (b) under anhydrous conditions sufficient to generate a new stereospecific phosphonate linkage in a new 5'-terminal nucleotide;

(h) repeating steps (b) through (g) one or more times to extend said oligonucleotide to the desired length; and (i) optionally removing the protecting group from the new 5'-terminal nucleotide.

DETAILED DESCRIPTION OF THE INVENTION

The present invention is directed to a process for synthesizing oligonucleotides with any desired stereo-specific substituted phosphonate linkage in a synthetic DNA or RNA analog on a solid phase support.

Control of backbone stereochemistry represents one of the major barriers to development of DNA and RNA therapeutics. The process described herein makes it possible to produce sufficient quantities of stereo-specific substituted phosphonates for diagnostic and therapeutic use.

The substitution of one of the nonbridging oxygens in the phosphodiester bond generates a chiral phosphate which can exist in two stereoconfigurations, namely equatorial and axial. The term "stereospecific linkage" designates a substituted phosphonate linkage which is predetermined to be either equatorial or axial. The term further refers to a linkage in which the stereoconfiguration of the phosphonate is controlled.

The process of this invention differs from the published method of Stec et al., "Stereospecific Synthesis of P-Chiral Analogs of Oligonucleotides", Chapter 14 in *Methods in Molecular Biology*, 20: *Protocols for Oligonucleotides and Their Analogs, Synthesis and Properties*, Agrawal, S. (ed.), Humana Press, Totowa, N.J., 285–313 (1993), in that the synthesis is carried out in the solid phase, suitable for automation, rather than in solution. In solution, each intermediate nucleotide must be purified chromatographically before proceeding to another coupling step. Moreover, Stec et al. admit that the liquid phase method is laborious because of the necessity of purification of intermediates. See Stec et al., supra at page 288. This tedious purification of intermediates is avoided in the solid phase synthesis method according to the present invention. The method produces oligonucleotides of the size and quantity necessary for exploiting antisense therapeutic technology.

Moreover, prior to this invention, the synthesis of oligonucleotides by solid phase synthesis has relied upon porous solid supports such as silica, controlled pore glass (CPG), or porous polystyrene beads or particles.

Oligomer synthesis takes place within the particle pores. The pores have an average diameter of 50–100 nm. Successful oligomerization depends on the rapid diffusion of reactants into and through the pores. Although the typical reactants used for phosphoramidite oligonucleotide synthesis are capable of rapid diffusion through 50–100 nm pores to enable nucleotide coupling, support losses occur at each intermediate purification step. Bonora et al., *Nucleic Acids Res.* 21: 1213–1217 (1993). Ultimate yields of oligomers with 10–20 nucleotides prepared by the porous particle method are therefore low.

The Grignard reagent-mediated oligomer synthesis method of Stec et al. (1993), supra, cannot be utilized with solid supports of the invention because of the high viscosity Grignard regent solutions. Grignard reagents will not diffuse into porous polymers at a rate high enough to support rapid oligonucleotide synthesis.

To circumvent the limitations of the prior art, the present invention utilizes a solid support for oligonucleotide synthesis in which the nascent oligomer is attached to the solid support outer surface. Because the oligomerization reaction is carried out on the particle outer surface and not within the confines of narrow pores, a Grignard reagent may be utilized to couple the 5'-deprotected terminal nucleoside in the growing oligomer chain. The use of a solid support such as polyethylene glycol coated polystyrene, enables efficient, rapid and stereospecific synthesis of oligomers containing substituted phosphonate linkages via a pentavalent Grignard coupling route. Additionally, the Grignard reagent does not interfere with the use of a precipitable soluble support as contemplated by another embodiment of the present invention.

The process described here begins with a 5'-protected nucleoside, e.g., a 5'-dimethoxytrityl (DMT) protected nucleoside, having a chemical linker at the 2' or 3' position coupled to a solid support. The solid support advantageously comprises for example a polyethylene glycol (PEG) coated polystyrene. The protecting group is removed by brief acid treatment, after which the exposed 5'-hydroxyl is activated with a Grignard reagent. After activation is complete, a pure diastereoisomer of a 5'-protected nucleotide having a substituted 3' phosphonate group is added to the support bound nucleoside. One non-bridging oxygen atom of the 3'-phosphonate group in the nucleotide has been replaced by a radical M and the remaining non-bridging oxygen has been coupled to a leaving group. Rapid coupling of the activated 5'-hydroxyl group of the support bound nucleoside to the phosphorous atom of the 5'-protected nucleotide ensues, releasing the leaving group to yield the equatorial or axial dimer. Rapid coupling avoids P-epimerization of the monomer and racemization of the dimer. The cycle is then repeated to yield a trimer. The cycle can be repeated as many times as desired, with whatever base is desired at each position, until an oligonucleotide of the desired length is achieved. The oligonucleotide is then cleaved from the solid support, deprotected and purified, yielding a substituted phosphonate nucleotide of defined stereochemistry at each linkage.

The process of the present invention provides oligomers with stereospecific alkyl, aryl, thio, borano or amino phosphonate linkages which replace the phosphodiester (—O—$PO_2$—O—) internucleotide linkage of unmodified oligonucleotides. M is selected from lower alkyl, cycloalkyl, thio, lower thioalkyl, aryl, aryl lower alkyl, borano, $BH_3$, $BF_3$, lower boranoalkyl, amino, aminoalkyl and dialkyl amino, wherein such lower alkyl and aryl groups can be substituted with at least one hydroxy, halogen or cyano group.

As used herein the term "lower alkyl" means an alkyl group containing one to ten carbon atoms. The carbon atom chain can be straight or branched, and includes, for example, such moieties as methyl, ethyl, propyl, isopropyl, n-butyl, sec-butyl, isobutyl, t-butyl, pentyl, amyl, hexyl and the like. Preferred lower alkyl groups have from one to five carbon atoms. The most preferred lower alkyl group is methyl.

As used herein, the term "cycloalkyl" means a saturated cyclic structure, i.e., a ring, having three to seven ring carbon atoms and includes, for example, such groups as cyclopropyl, cyclobutyl, cyclopentyl, cyclohexyl and cycloheptyl rings.

By "thio lower alkyl" is meant a lower alkyl attached to a sulfur atom.

By "aryl" is meant an aromatic moiety containing five to ten ring carbon atoms. The term includes phenyl, α-naphthyl, β-naphthyl, and the like. Phenyl is a preferred aryl group.

Preferred substituents M include lower alkyl, phenyl and phenyl substituted with one or more halogen atoms, preferably a fluorine. Methyl is particularly preferred.

The nucleotides joined according to the present invention comprise deoxyribonucleotides and ribonucleotides as well as derivatives thereof. A listing of such derivatives may be found in Knorre et al, Chapter 3, "Oligonucleotide Synthesis", *Design and Targeted Reactions of Oligonucleotide Derivatives*, in CRC Press, Boca Raton, Fla., 101–146 (1994), the entire disclosure of which is incorporated herein by reference. Nucleotides may be joined at either the 2' or 3' position to generate oligomers having either 2'-5' or 3'-5' linkages, respectively.

The nucleotides linked according to the present invention contain a B group which represents the base moiety present on the nucleotide. The phrase "substituted or unsubstituted purine and pyrimidine base" means the purine bases guanine and adenine, and the pyrimidine bases, thymine, cytosine and uracil, and any related base analog that is capable of base pairing with guanine, adenine, thymine, cytosine or uracil, or any derivative of said bases. For examples of such bases, see Knorre et al., "Oligonucleotide Synthesis", Chapter 3 in *Design and Targeted Reactions of Oligonucleotide Derivatives*, CRC Press, Boca Raton, Fla., 101–146 (1994) and Wickstrom et al., Intl. Publication No. WO 94/00473, 13–15 (6 Jan. 1994), the entire disclosures of which are incorporated herein by reference.

Preferred B groups are unmodified G, A, T, C and U bases. In addition, preferred B groups include pyrimidines and purines with lower alkyl, lower alkoxy, lower alkylamine, phenyl or lower alkyl substituted phenyl groups. It is more preferred that these groups are present on the 5 position of the pyrimidine and on the 7 or 8 position of the purine. Especially preferred base analogs are 5-methylcytosine, 5-methyluracil and diaminopurine.

The base moiety may also comprise a protected purine or protected pyrimidine base, $B^a$. The protecting group may comprise any chemical group attached to an exo-cyclic amine group which prevents the amine group from reacting during an internucleotide bond formation reaction. The protecting groups are attached, for example, at $N^6$ in adenine, $N^2$ in guanine and $N^4$ in cytosine. Preferred protecting groups include isopropyl, isobutyryl, 2-cyanoethyl, acetyl, benzoyl, phenoxyacetyl, halophenyl, dimethoxytrityl and monomethoxytrityl.

Moreover, the selection of a B group for each nucleotide added to the growing polynucleotide chain determines the nucleotide sequence of an oligonucleotide produced by the present method. Accordingly, the present method can be used to generate oligonucleotides having any desired nucleotide sequence by varying which nucleotide base B is placed at each position. The selection of a nucleotide sequence is generally determined by the intended purpose of the oligonucleotide.

The oligonucleotides according to the present invention may comprise n+2 nucleotides, wherein n is zero to 200. When n is 0, a single stereospecific substituted phosphonate linkage is formed, and the product constitutes a dinucleotide. The present invention is directed towards application of the subject method to form isolated stereospecific substituted phosphonate linkages as well as sequential chains of stereospecific substituted phosphonate linkages.

In a preferred embodiment the present invention is directed to an oligonucleotide having at least five sequential nucleotides (i.e., n=3) having equatorial stereospecific substituted phosphonate linkages produced by the pentavalent Grignard coupling method described herein. It is desirable to have a method that can make oligomers containing 5 or more nucleotides having stereospecific substituted phosphonate linkages. Oligomers of 8 or more nucleotides are desirable where the oligomer is hybridized to a target nucleotide sequence, such as in the case of therapeutic antisense oligonucleotide. More preferably, oligonucleotides for use in hybridization will contain at least about 10, more preferably 12, nucleotides. Oligomers of up to 200 nucleotides and larger may be prepared according to the practice of the present invention.

According to the present invention, $Y_1$ is present on the 2' or the 3' oxygen of a nucleoside, and can be a hydrogen or $V_1$, where $V_1$ is a solid support or precipitable soluble polymer. While the preparations and examples described herein illustrate the synthesis with a 3'-5' linkage, the synthesis described is equally applicable for 2'-5' linkages. The synthesis for a 2'-5' linkage would simply require the substitution of appropriate nucleoside-2'-phosphates for nucleoside-3'-phosphates.

According to one embodiment of the invention, $V_1$ is a solid support which anchors the growing polynucleotide chain. $V_1$ may comprise any solid support suitable for oligonucleotide synthesis. Appropriate types of solid supports include polyacrylate, latex, polystyrene, and high-loaded polystyrene which is a polyethylene glycol coated polystyrene. The aforesaid high-loaded polystyrene support used in the hereinafter examples was prepared from low cross-linked (1% divinylbenzene) polystyrene and is commercially available from Perkin Elmer/Applied Biosystems as HLP.™ The support contains surface groups of the formula

wherein i is approximately 70.

The solid support is covalently linked to the 2'-OH or a 3'-OH of a nucleoside by known procedures, for example, Matteucci et al., *Tetrahedron Lett.* 21: 719–722 (1980) or Bonora et al., *Nucleic Acids Research*, 21: 1213–1217 (1993), with resort to any one of numerous linking groups. The most commonly employed linking group is succinate. For a general discussion of solid phase supports and linkers, see *Oligonucleotide Synthesis: A Practical Approach*, Gait, Michael J. (ed.), IRL Press, Oxford, 1–22 (1984). Alternatively, nucleosides linked to solid supports having a reactive outer surface can be purchased commercially, as for example from Perkin-Elmer/Applied Biosystems. Following the completion of oligomer synthesis, the having a reactive outer surface solid support may be easily removed from the oligonucleotide by conventional known procedures, e.g. by alkaline hydrolysis, Hogrefe et al., *Methods in Molecular Biology, Vol.* 20: *Protocols for Oligonucleotides and Their Analogs, Synthesis and Properties*, Humana Press, Totowa, N.J., 143–164 (1993).

The invention herein is equally applicable to oligomer synthesis utilizing a precipitable soluble polymer as a support. As used herein, a precipitable soluble polymer is a polymer capable of being precipitated out of solution by adjusting the prevailing solvent conditions, or substituting a different solvent. The precipitable soluble support allows for easy purification of oligomer intermediates after each addition of a nucleotide. An example of a suitable precipitable polymer is polyethylene glycol (PEG) having a molecular weight ranging from about 4,000 g/mole to about 35,000 g/mole, and preferably from about 4,000 g/mole to about 12,000 g/mole. PEG in the appropriate size range is commercially available from chemical suppliers such as Aldrich Chemical or Fluka.

Oligomer synthesis proceeds by sequential addition of 5'-protected nucleotides to the growing nucleotide chain.

The nucleotides bear a protecting group $V_2$ which renders the 5' oxygen of the nucleotide unreactive while the present synthetic methods are performed. Ideally, a protecting group is easily removed to regenerate the correct structure of the reactive group without chemically altering the remainder of the molecule.

Examples of protecting groups include any known blocking or protecting agent used during synthesis of deoxyribonucleotides or ribonucleotides to protect a hydroxy group, e.g. a 5'-OH, 3'-OH or 2'-OH group. The $V_2$ protecting group is preferably attached via an oxygen atom. In this regard, Greene et al., *Protecting Groups in Organic Synthesis*, John Wiley & Sons, Inc. (1991) provides a comprehensive review of protecting groups which can be used for different organic reactive groups, including OH reactive groups.

Preferred protecting groups include lower alkyl, lower cyanoalkyl, lower alkanoyl, aroyl, aryloxy, aryloxy-lower alkanoyl, haloaryl, fluorenylmethoxy carbonyl (FMOC), trityl, monomethoxytrityl (MMT), dimethoxytrityl (DMT), and related groups. More preferred protecting groups include isopropyl, isobutyryl, isobutyl, 2-cyanoethyl, acetyl, benzoyl, phenoxy-acetyl, halophenyl, MMT, DMT and the like.

Leaving group L is defined as a group which is readily broken away from a covalent linkage by nucleophilic attack on that atom. Leaving groups are generally electron withdrawing groups either because of their electronegativity or because they have an inductive effect. Typically leaving groups include, but are not limited to, nitrophenyl, chlorophenyl, fluorenylmethoxy carbonyl, succinimidyl, or any weak nucleophiles. Such weak nucleophiles are commonly known to those skilled in the art. The preferred leaving group for this invention is 4-nitrophenyl.

According to the practice of the invention, the 5'-protected-3'-O-succinyl monomer of Formula I or Ia is reacted with a Grignard reagent. The Grignard reagent is any alkylmagnesium halide. There are numerous commercially available Grignard reagents including, but not limited to, allylmagnesium bromide, benzylmagnesium chloride, tert-butylmagnesium chloride, isobutyl magnesium bromide and phenylmagnesium chloride. A listing of typical Grignard reagents can be found on pages 1758–1759 of the 1994–1995 Aldrich Chemical catalog, which is incorporated herein by reference. Any of these agents may be used in the practice of the invention.

According to the practice of this invention, the first (or 5') nucleoside is reacted with the stereospecific monomer of formula II or IIa under conditions sufficient to covalently link the 5'oxygen of the 5'-terminal nucleoside with the substituted phosphonate, and thereby displace the leaving group L. This inverts the axial stereoconfiguration to produce the equatorial substituted phosphonate linkage, or vice versa.

As used herein, conditions sufficient to covalently link the 5'-oxygen with the Formula II or IIa monomer include those time, temperature, solvent and reactant concentration conditions permitting nucleophilic attack by the 5'-oxygen upon the phosphorus atom of the substituted phosphonate linkage to displace the leaving group L and invert the substituted phosphonate linkage.

A time sufficient to covalently link the 5'-oxygen with the Formula II or IIa monomer is about 1 hour to about 10 hours, and preferably about 1 hour to about 5 hours.

The reaction temperature preferably employed for the coupling reaction is about 0° C. to about 40° C. A more preferred reaction temperature is about 4° C. to about 35° C. An especially-preferred coupling temperature is about room temperature, i.e., about 20° C. to 25° C.

The reaction solvent conditions for coupling the 5' oxygen of the 5'-terminal nucleoside to the Formula II or IIa monomer are anhydrous conditions, wherein a nonpolar or nonpolar aprotic solvent is employed. Preferred solvents for use during of coupling include acetonitrile, dimethylformamide, tetrahydrofuran, dimethylsulfoxide, pyridine and the like.

According to the present invention, the molar ratio of 5'-deprotected nucleoside relative to the 5'-protected stereospecific nucleotide can range from about 1:10 to about 1:1. Preferably the molar ratios are about 1:5 to about 1:1. An especially preferred molar ratio about 1:5.

The invention contemplates that $V_1$ can be either a solid support or a precipitable soluble polymer. Reaction conditions sufficient to generate the stereospecific substituted phosphonate linkage using a precipitable soluble polymer are the same as those for the solid support with the exception of the need for an additional precipitation/purification step for the precipitable soluble polymer embodiment after the addition of each nucleotide. To that end, after the coupling reaction is complete, the solvent is changed and/or the solvent conditions adjusted so that the reaction product, i.e., growing oligomer, is precipitated out of solution. After precipitation, the purified product is then redissolved in the appropriate solvent to continue the coupling of additional stereospecific monomers. Solvents suitable for the precipation of the product include, but are not limited to, diethyl ether, ethanol, and all other commercially available solvents in which PEG is not soluble.

Schemes 2 and 3 that follow below exemplify one overall reaction scheme for the coupling of a monomer on a support (Formula I or Ia) to a stereospecific monomer (Formula II or IIa) to form a dimer nucleotide. The details of the coupling reaction are given below in Example 1 for forming compounds 8 and 9, and in Example 3 for forming compounds 14 and 15. After purification, the protected dimer 8 or 9, is deprotected according to Preparation 5, and oligomer synthesis is continued by repeating Example 1 for each additional nucleotide until the desired chain length is achieved. Final deprotection and cleavage from the support is performed according to Example 2. Analogously, after purification, the protected dimer 14 or 15 is deprotected according to Preparation 7 and oligomer synthesis is continued by repeating Example 3 and final deprotection according to Example 4.

According to the present invention, conditions sufficient to produce the Grignard intermediate of the invention include nuclear displacement conditions wherein the 5'-hydrogen of the monomer on the support is displaced by the metal atom of the Grignard reagent. Such conditions include a time, a solvent, a temperature and a reactant concentration sufficient for such nucleophilic displacement of the hydrogen by the magnesiumalkyl halide.

A time sufficient to displace the hydrogen and so produce the intermediate is about 30 minutes. The preferred solvent for generating the Grignard-nucleoside intermediate is an anhydrous solvent, and preferably is tetrahydrofuran or pyridine. The temperature preferably employed to displace the hydrogen with the metal atom, and thereby form the intermediate, is about 0° C. to about 60° C. A more preferred displacement temperature is about 4° C. to about 40° C. An especially preferred temperature for forming the intermediate is about room temperature, i.e., about 20° C.

The invention method described herein can produce oligonucleotides having at least 90% of the desired stereospecific substituted phosphonate linkages in an oligonucleotide. More particularly, the oligonucleotides generated by the present method have about 95% to about 100% stereospecific substituted phosphonates linkages.

More importantly, while others have reported methods having similar levels of stereospecificity of coupling, none have reported the yields described herein. For example, Stec et al., "Stereospecific Synthesis of P-Chiral Analogs of Oligonucleotides", Chapter 14 in *Methods in Molecular Biol. Vol.* 20: *Protocols for Oligonucleotides and Analogs*, Agrawal, S. (ed.), Humana Press, Totowa, N.J., 285–313 (1993), reports couplings in the 95% range, but with yields around 60%. The lower yield is a consequence of the liquid phase nature of the oligomer synthesis, which requires purification of intermediate products after the addition of each nucleotide, resulting in declining yields with each additional nucleotide.

The invention described herein is readily adaptable to automation in a nucleic acid synthesizer. Nucleic acid synthesizers that could be utilized include, but are not limited to, the Millipore Model 8800 synthesizer for large scale synthesis (at the 100 μm to 1000 μm level), the Millipore Model 8750 synthesizer for small scale synthesis (1 μm to 15 μm) or the Applied Biosystems Model 390Z synthesizer (25 μm up to 1 mm). To automate the synthesis described herein, one would utilize the simple expedient of writing an appropriate computer program for the synthesizer to control the valve openings and closings (to add reagents) to correspond to the present invention reaction times and sequences. However, it is not anticipated that any variation would be necessary to the chemical synthesis described herein to adapt it for use on a synthesizer. Room temperatures, solvents and the reagents would be consistent with the present invention.

According to the present invention, equatorial stereospecific oligonucleotide products derived from the subject synthetic method can have an attached agent to facilitate cellular delivery or uptake. Such an agent can, for example, be any known moiety which enhances cellular membrane penetration by the oligonucleotide, any known ligand for a cell-specific receptor or any available antibody reactive with a cell-specific antigen.

A moiety or ligand which enhances cellular membrane penetration by the oligonucleotide can include, for example, any non-polar group, steroid, hormone, polycation, protein carrier, or viral or bacterial protein carriers capable of cell membrane penetration. For example, the covalent linkage of a cholesterol moiety to an oligonucleotide can improve cellular uptake by five to ten fold which in turn improves DNA binding by about ten fold, Boutorin et al., *FEBS Letters* 254: 129–132 (1989). Polycations, such as poly-L-lysine, can also facilitate uptake of oligonucleotides into cells, Schell et al., *Biochem. Biophys. Acta* 340: 323 (1974) and Lemaitre et al., *Proc. Natl. Acad. Sci. USA* 84: 648 (1987). Accordingly, the present invention contemplates derivatization of the subject oligonucleotides with the above-identified groups to increase oligonucleotide cellular uptake.

The present invention contemplates a variety of utilities for the subject Rp stereospecific oligonucleotides. Some utilities include, but are not limited to: use of oligonUcleotides of defined sequence bound to a solid support for affinity isolation of complementary nucleic acids; covalent attachment of a drug, drug analog or other therapeutic agent to the oligonucleotide to allow cell-type specific drug delivery; labeling the subject oligonucleotides with a detectable reporter molecule for localizing, quantitating or identifying complementary target nucleic acids; and binding oligonucleotides to a cellular or viral nucleic acid template and regulating biosynthesis directed by that template.

Moreover, the present invention also contemplates the preparation of stereospecific substituted phosphonate linkages in oligonucleotides having any nucleotide sequence. In many instances the selection of a nucleotide sequence depends upon the intended purpose of the oligonucleotide. For example, the nucleotide sequence can be selected for the purpose of binding to a nucleic acid target present within a template nucleic acid or to detect or to regulate the biosynthesis of such a template nucleic acid. For a more thorough discussion of the use of oligonucleotides having stereospecific substituted phosphonate linkages with respect to DNA templating, replication, transcription and regulation of biosynthesis, reference is made to Wickstrom et al., Intl. Publication No. WO 94/00473 (6 Jan. 1994), the entire disclosure of which is incorporated herein by reference.

Some types of genetic disorders that can be treated by DNA therapy utilizing the stereospecific substituted phosphonated oligonucleotides of the present invention include, in a nonexclusive list the following:

(a) Cancer: A wide variety of modes of uncontrolled cell growth fall under the umbrella name of cancer. Solid tumors and leukemias exhibit mutational activation or overexpression of a family of proliferative genes called oncogenes, as well as inactivation or underexpression of suppressor genes Bishop, J. M., *Cell* 64: 231–248 (1991). In those instances where the malignant state is maintained by identifiable oncogene or proto-oncogene products, cell transformation may be reversed, and the cell returned to normal, by DNAs directed against the active oncogenes, Wickstrom et al., *Cancer Research* 52: 6741–6745 (1992); Gray et al., *Cancer Research* 53: 577–580 (1993).

(b) Viral Infections: During viral infection of a cell, DNAs directed against viral-specific gene products may prevent viral replication and production, thereby stopping the disease in an unvaccinated individual. Human immunodeficiency virus, herpes simplex virus, and influenza virus are examples of virus to which is is expected this invention will be directed.

(c) Autoimmune Diseases: Inadvertent production of antibodies against normal body tissues and structures results in degeneration of the target tissue, Davis, M. M., *Annu. Rev. Biochem.* 59: 475–496 (1990). DNAs complementary to unique sequences in the autoimmune B-cell immunoglobulin genes or T-cell receptor genes may be capable of suppressing production of the autoimmune antibodies or receptors by the particular plasma cell clonal lines involved. This approach may be of value in treating arthritis, lupus erythromatosus, and myasthenia gravis, among others. DNA chemotherapy may also be of value in suppressing the graft rejection response without compromising an individual's entire immune system.

(d) Endocrinological Diseases: Elevated blood pressure results from abnormal levels of renin angiotensinase, or the precursor of vasopressin, depending on the individual involved. Barrett et al., *Proc. Natl. Acad. Sci. USA* 89: 885–889 (1990). DNA chemotherapy to reduce production of these peptides may therefore improve the management of hypertension. DNA chemotherapy may also be of value in reducing the production of any other peptide hormone which is being produced in excess and thereby causing health problems. Examples include transforming growth factor a, in the case of kidney failure, growth hormone, in the case of acromegaly, and gastrin, in the case of ulcers, Border et al., *Nature* 346: 371–374 (1990).

(e) Neurological Diseases: Alzheimer's disease may in some cases be due to genetic lesions in the gene for β-amyloid protein, Hardy et al., *Lancet* 337: 1342–1343 (1991). Hence, DNA therapeutics specific to the mutant allele may hold disease in check or prevent its onset. Similarly, overly abundant monoamine oxidase has been implicated in some varieties of mental illness, Georgotas et al., *Psychiatry* 19: 247–286 (1986). DNA chemotherapy to reduce monoamine oxidase production may be a more specific treatment, with fewer detriments to other neural functions, than current medications.

(f) Bacterial infections: DNAs complementary to the 3' terminus of prokaryotic 16S rRNA have been synthesized, and found to inhibit mRNA translation by direct competition for ribosomes, Jayaraman et al., *Proc. Natl. Acad. Sci. USA* 78: 1537–1541 (1981). Hence, such DNAs may be exploited as a new class of antibiotics. These may be very valuable against strains of tuberculosis resistant to all known antibiotics, Goldsmith, J. F., *J. Amer. Med. Assoc.* 264: 165–166 (1990), or mycoplasmas thought by some to be synergistic in HIV infection, Lo et al., *Science* 251: 1074–1076 (1991).

(g) Parasites: Malaria debilitates its victims, and escapes the immune system by frequent mutation. *Plasmodium falciparum* trophozoites express a haem polymerase which concentrates toxic free haem into a nontoxic hemozoin granule, Slater et al., *Nature*, 355: 167–169 (1992). This enzyme is inhibited by chloroquine, quinine and their relatives; the enzyme is mutated in chloroquine-resistant strains of malaria. DNA therapeutics targeted against a conserved sequence of the haem polymerase gene may provide a weapon against malarial strains resistant to existing drugs. Similarly, trypanosomes, the cause of sleeping sickness, evade the immune system, and develop drug resistance. Their utilization of a common 35 nucleotide leader on their messengers provides an excellent opportunity for antisense DNA intervention, Cornelissen et al., *Nucleic Acids Res.* 14: 5605–5614 (1986).

Preparation of the compounds of the present invention is illustrated in more detail by reference to the following non-limiting examples.

Materials and Methods

Polyethylene glycol monomethylether (PEG$_{4600}$) used in the preparations was purchased from Aldrich. The high-loaded polystyrene support (HLP) was obtained from Perkin-Elmer/Applied Biosystems and the protected 5'-dimethoxytrityl (DMT)-deoxynucleosides were purchased from Glen Research. All reagents and anhydrous solvents, of the highest commercially available purity, were purchased from Aldrich and used without further purification.

Merck silica gel 60 F$_{254}$ plates were used for analytical thin layer chromatography (TLC), and the separated compounds were detected by absorption of ultraviolet (UV) light from a 254 nm Mineralight UV source, or Dische acid spray. Purification of the compounds was done by liquid chromatographic techniques carried out on a Chromatotron chromatogram by Harrison Research Ltd., using plates prepared from Merck silica 60 PF$_{254}$ type 7749. Analytical high performance liquid chromatography (HPLC) was performed on a Waters 600 column with an Econosphere silica gel (5 μm) column (1×25 cm). All $^1$H nuclear magnetic resonance (NMR) spectra were recorded on a Bruker 600 AMX spectrometer using tetramethylsilane as an internal standard. Similarly, $^{31}$P NMR spectra were recorded with the same instrument using dimethyl methylphosphonate as an external standard in CDCl$_3$ (32.4 ppm from H$_3$PO$_4$).

Scheme 1, which corresponds to Preparations 1 and 2, represents the phosphorylation of the 5'-protected nucleoside with the substituted phosphonate to form the stereospecific monomer, compounds 1 and 2 (purine base) and 3 and 4 (pyrimidine base).

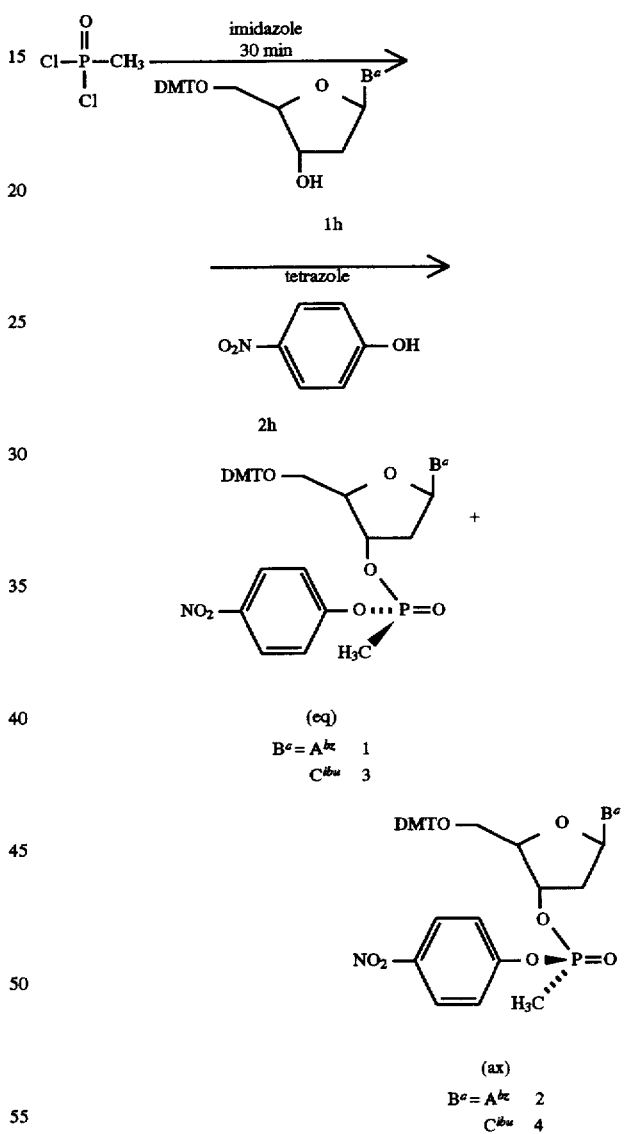

Preparation 1

5'-O-Dimethoxytrityl-N$^6$-benzoyl-2'-deoxyadenosine-3'-O-(O-(4-nitrophenyl)methylphosphonate 1 and 2

To begin the preparation of the titled compound, imidazole (830 mg; 12 mmol) was added to a solution of methylphosphonic dichloride (325 mg; 2.44 mmol) in anhydrous pyridine (12 ml). The reaction was stirred at room temperature for 30 min, and then 5'-O-dimethoxytrityl-N⁶-benzoyl-2'-deoxyadenosine (1.6 g; 2.43 mmol) dissolved in anhydrous pyridine (4 ml) was added. The progress of the reaction was monitored by TLC (CH₂Cl₂/MeOH; 92.5:7.5), and after 60 to 90 min, tetrazole (620 mg, 8.76 mmol) and 4-nitrophenol (305 mg; 2.19 mmol) were added. After 2 hours (TLC monitoring; CH₂Cl₂/MeOH; 92.5:7.5), the reaction mixture was diluted with CH₂Cl₂ (100 ml), washed with saturated aqueous NaHCO₃, then water, dried over sodium sulfate, and concentrated under vacuum. The oily residue was purified by liquid chromatography on silica gel with CH₂Cl₂/MeOH (97:3) to give Eq-isomer 1 (670 mg; 0.78 mmol; 32%) and followed with CH₂Cl₂/MeOH (95:5) to give Ax-isomer 2 (520 mg; 0.61 mmol; 25%). The separation of each isomer was monitored by TLC (CH₂Cl₂/MeOH, 92.5:7.5), and analytical silica gel HPLC with a gradient of 0–10% of MeOH in CHCl₃ over 20 min at a flow rate of 5 ml/min. Following the conventions set forth in Stec et al., "Stereospecific Synthesis of P-Chiral Analogs of Oligonucleotides", Chapter 14 in *Methods in Molecular Biology*, Vol. 20, "Protocols for Oligonucleotides and Their Analogs, Synthesis and Properties", Humana Press, Totowa, N.J., 285–313 (1993), the faster eluting compound 1 was assigned to the Eq-isomer and the slower eluting compound 2 to the Ax-isomer. Assignment data: Eq-isomer 1: Rf=0.69 (CH₂Cl₂/MeOH, 92.5:7.5). Rt=6.35 min on HPLC. ³¹P NMR (CDCl₃): 28.84 ppm. Ax-isomer 2: Rf=0.71 (CH₂Cl₂/MeOH, 92.5:7.5). Rt=7.67 min on HPLC. ¹H NMR (CDCl₃): 1.82 (d, 3H, P—CH₃); 2.85 (dd, 1H, H2'); 3.15 (d, 1H, H2"); 3.33 (dd, 1H, H5'); 3.47 (dd, 1H, H5"); 3.80 (2s, 6H, OCH₃); 4.36 (m, 1H, H4'); 5.33 (m, 1H, H3'); 6.58 (t, 1H, H1'); 6.79–7.64 (m, 13H, aromatic protons of DMT); 8.06 (d, 2H, protons of 4-nitrophenyl); 8.18 (d, 2H, protons of 4-nitrophenyl); 8.74 (s, 1H, H8); 9.23 (s, 1H, H2). ³¹P NMR (CDCl₃): 28.72 ppm.

Preparation 2

5'-O-Dimethoxytrityl-N⁴-isobutyryl-2'-deoxycytidine-3'-O-(O-(4-nitrophenyl)methylphosphonate 3 and 4

Analogous to preparation 1, the Eq-isomer 3 and Ax-isomer 4, utilizing a pyrimidine base, were prepared using methylphosphonic dichloride (200 mg; 1.5 mmol), 5'-O-dimethoxytrityl-N⁴-isobutyryl-2'-deoxycytidine (1 g; 1.67 mmol) and 4-nitrophenol (240 mg; 1.72 mmol). After purification by liquid chromatography on silica gel with CH₂Cl₂/MeOH (97:3), compounds 3 (335 mg; 0.42 mmol; 25%) and 4 (270 mg; 0.34 mmol; 20%) were obtained. The faster eluting compound 3 was again assigned to the Eq-isomer and the slower eluting compound 4 to the Ax-isomer. Assignment data: Eq-isomer 3: Rf=0.56 (CH₂Cl₂/MeOH, 92.5:7.5). ¹H NMR (CDCl₃): 1.20 (m, 6H, CH₃ of ibu); 1.64 (d, 3H, P—CH₃); 2.61 (m, 1H, H2'); 2.59 (m, 1H, H2"); 2.78 (m, 1H, CH of ibu); 3.48 (m, 1H, H5'); 3.73 (m, 1H, H5"); 3.80 (2s, 6H, OCH₃ of DMT); 4.40 (m, 1H, H4'); 5.23 (m, 1H, H3'); 6.27 (t, 1H, H1'); 6.80–7.40 (m, 15H, H5, H6 and aromatic protons of DMT); 8.08 (d, 2H, protons of 4-nitrophenyl); 8.25 (d, 2H, protons of 4-nitrophenyl). ³¹P NMR (CDCl₃): 29.19 ppm. Ax-isomer 4: Rf=0.46 (CH₂Cl₂/MeOH, 92.5:7.5). ¹H NMR (CDCl₃): 1.18 (m, 6H, CH₃ of ibu); 1.76 (d, 3H, P—CH₃); 2.36 (m, 1H, H2'); 2.64 (m, 1H, H2"); 2.92 (m, 1H, CH of ibu); 3.31 (m, 1H, H5'); 3.59 (m, 1H, H5"); 3.76 (s, 6H, OCH₃ of DMT); 4.22 (m, 1H, H4'); 5.28 (m, 1H, H3'); 6.30 (t, 1H, H1); 6.80–7.40 (m, 15H, H5, H6 and aromatic protons of DMT); 8.05 (d, 2H, protons of 4-nitrophenyl); 8.16 (d, 2H, protons of 4-nitrophenyl). ³¹P NMR (CDCl₃): 29.59 ppm.

Scheme 2 begins the preparation of the heterodimer on the precipitable soluble polymer, PEG. In Preparation 3 the purchased 5'-protected nucleoside is attached to the succinate linker, 5, which in turn is attached to the precipitable soluble polymer in Preparation 4, 6. The scheme continues with the coupling of the deprotected monomer on the support, 7, with the stereospecific monomer, 1 or 2, in Example 1, followed by the deprotection and cleavage from the support in Example 2. While the coupling reaction is shown only for illustration purposes with monomers 1 and 2, the same reaction scheme is used to couple any stereospecific 5'-protected nucleotide.

Scheme 2

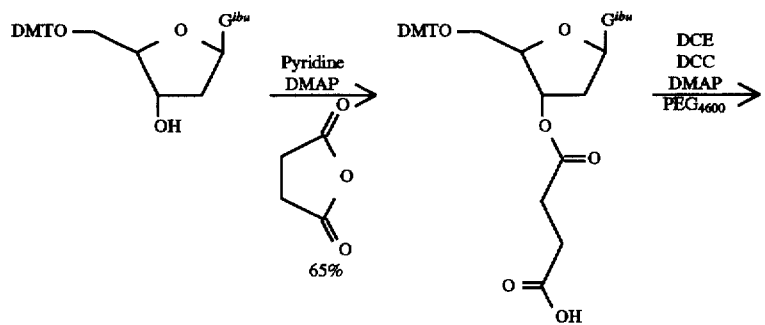

27

-continued
Scheme 2

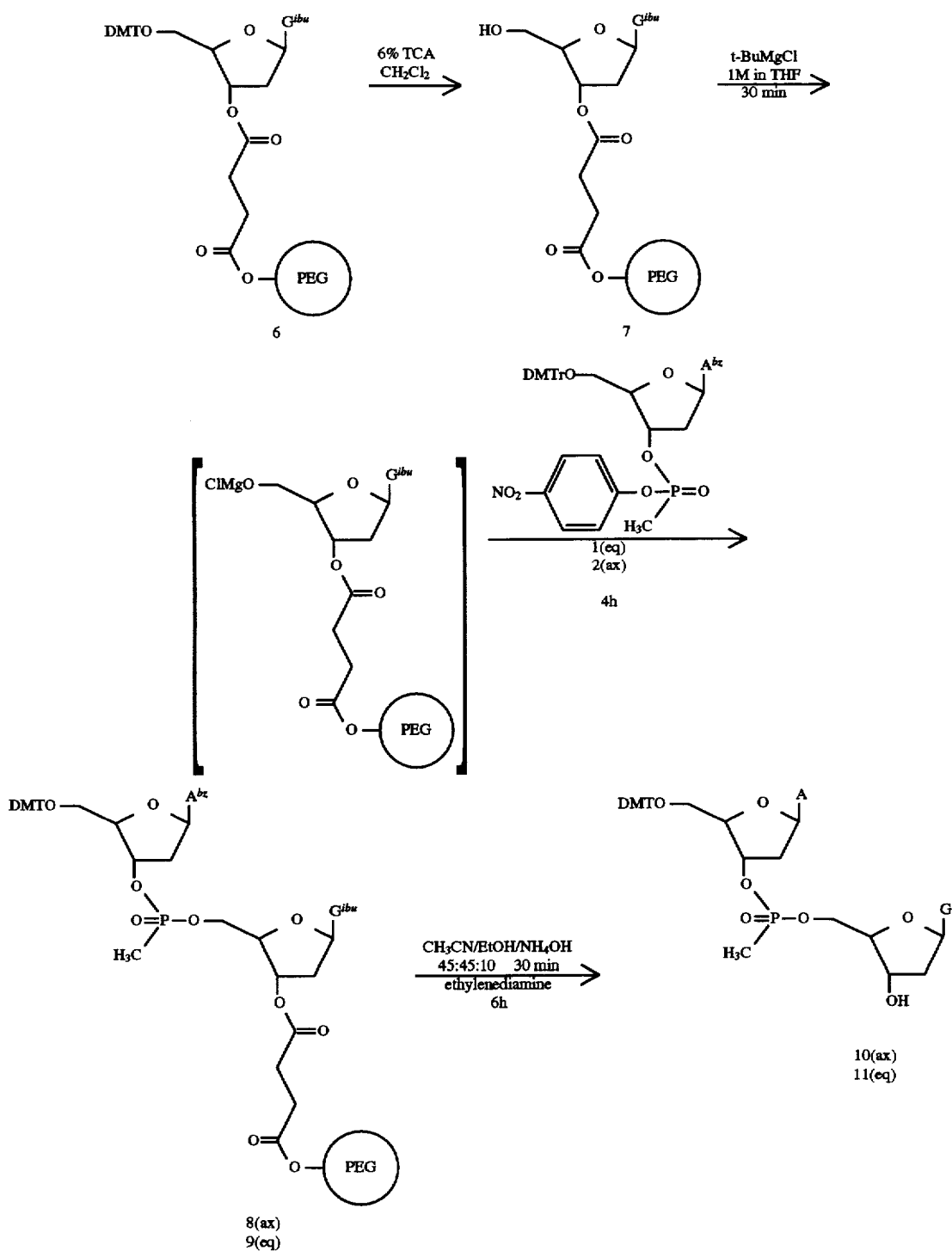

Preparation 3

5'-O-Dimethoxytrityl-N²-isobutyryl-3'-O-succinyl-2'-deoxyguanosine 5

5'-Dimethoxytrityl-2'-deoxyguanosine (1 g, 1.56 mmol) was coevaporated 3 times with 10 ml of dry pyridine and then dissolved in 10 ml of pyridine. Dimethylaminopyridine (190 mg, 1.56 mmol) and succinic anhydride (325 mg, 3.25 mmol) were added and the reaction mixture was stirred for 36 hours at room temperature. The mixture was evaporated under reduced pressure and the residue was diluted in 100 ml of $CH_2Cl_2$, washed with saturated aqueous $NaHCO_3$ and water. The organic phase was dried over $Na_2SO_4$ and concentrated. The oily residue was purified by liquid chromatography on silica gel with $CH_2Cl_2$/MeOH (90:10) to afford compound 5 (750 mg, 1.02 mmol, 65%); Rf=0.40 (CH$_2$Cl$_2$/MeOH, 90:10).

Preparation 4

5'-O-Dimethoxytrityl-N$^2$-isobutyryl-3'-O-succinyl-2'deoxyguanosine-PEG 6

Polyethylene glycol monomethylether (PEG$_{4600}$, 1.25 g, 0.27 mmol of free OH-groups) was coevaporated 3 times with anhydrous pyridine (10 ml) and dissolved in 12.5 ml of 1,2-dichloroethane (DCE) according to the method of Bonora et al., *Nucleic Acids Res.* 21: 1213-1217 (1993). The protected-3'-O-succinyl-2'-deoxyguanosine 5 (600 mg, 0.81 mmol) was dried by multiple coevaporation in anhydrous pyridine, then dissolved in 7 ml of DCE. Dicyclohexylcarbodiimide (100 mg, 0.45 mmol) was added under stirring at 0° C., and after 15 min the precipitate of dicyclohexyl urea was removed by filtration. The filtrate was poured into the PEG solution and dimethylaminopyridine (55 mg, 0.45 mmol) was added. The reaction mixture was concentrated to approximately 4 ml and left under stirring at room temperature for 20 hours. The solution was filtered and the polymer 6 was purified by precipitation alternatively with Et$_2$O and absolute ethanol, then dried overnight under vacuum over KOH pellets. The complete elimination of unreacted 5 was confirmed by TLC (ethyl acetate/acetone/H$_2$O, 10:5:1). The yield of the reaction was determined by measuring the DMT absorption at 504 nm; the loading value of deoxyguanosine of 6 corresponds to 140 µmol/g (1 g). The unreacted OH-groups of PEG were capped by treating with a solution containing 1 ml of 2,6-lutidine, 1 ml of N-methylimidazole and 1 ml acetic anhydride in 10 ml of CH$_3$CN. After 5 min at room temperature, the polymer 6 was precipitated at 0° C. with Et$_2$O and dried overnight under vacuum over KOH pellets (850 mg).

Preparation 5

N$^2$-Isobutyryl-3'-O-succinyl-2'-deoxyguanosine-PEG 7

Detritylation of the nucleoside was carried out by dissolving compound 6 (700 mg, 98 µmol) in 7 ml of CH$_2$Cl$_2$, and adding dropwise 7 ml of a solution of 6% trichloroacetic acid in CH$_2$Cl$_2$ while stirring vigorously at 0° C. After 15 min, the polymer 7 was precipitated with Et$_2$O, washed, filtered and dried over KOH pellets (650 mg). The complete elimination of the solution phase reagents was confirmed by TLC (ethyl acetate/acetone/H$_2$O, 10:5:1).

EXAMPLE 1

5'-O-Dimethoxytrityl-N$^6$-benzoyl-3'-O-methylphosphonate-2'-deoxyadenylyl-N$^2$-isobutyryl-3'-O-succinyl-2'-deoxyguanosine (Ax) 8 and (Eq) 9:

Example 1 outlines the procedure for the activation of the PEG-nucleoside and the coupling with a stereospecific monomer to form the heterodimer. To that end, using the procedure of Stec et al., "Stereospecific Synthesis of P-Chiral Analogs of Oligonucleotides", Chapter 14 in *Methods in Molecular Biology, Vol. 20: Protocols for Oligonucleotides and Their Analogs, Synthesis and Properties*, Humana Press, Totowa, N.J., 285-313 (1993), compound 7 (120 mg, 17 µmol) was dissolved in anhydrous pyridine (20 µl) and a solution of tert-butylmagnesium chloride in THF (1M, 70 µl, 70 µmol) was added. After 30 min, 15 mg (18 µmol) of either Eq-isomer 1 or Ax-isomer 2 in dry THF (100 µl) was added to the solution of 5'-OH-activated support. The reaction progress was monitored by TLC (ethyl acetate/acetone/H$_2$O, 10:5:1) and after 3 hours, some new product (Rf 0) appeared. Using the method of Bonora et al., *Nucleic Acids Res.* 21: 1213-1217 (1993), the reaction was stopped by precipitation of the support with an excess of Et$_2$O at 0° C., filtered, and rinsed with Et$_2$O to give a yellow gum, which was dissolved in CDCl$_3$ and analyzed by $^{31}$P NMR. The yield of the reaction of 71% (equivalent to 100 µmol/g) was determined by measuring DMT absorption at 504 nm. The yield of the PEG support after multiple precipitations was 85%. Assignment data: DMT-dA$^{bz}$p(Me,Ax)dG$^{ibu}$-PEG 8: $^{31}$P-NMR (CDCl$_3$): 22.97 ppm; DMT-dA$^{bz}$p(Me,Eq)dG$^{ibu}$-PEG 9: $^{31}$P-NMR (CDCl$_3$): 22.96 ppm.

To confirm the stereospecificity of the coupling reactions of each dimer-PEG 8 and 9, the products were identified by $^{31}$P NMR and by HPLC after deprotection of the base protecting groups and cleavage from the support as described in Example 2 that follows.

EXAMPLE 2

5'-O-Dimethoxytrityl-3'-O-methylphosphonate-2'-deoxyadenylyl-2'-deoxyguanosine (Ax) 10 and (Eq) 11

Using the method of Hogrefe et al., *Methods in Molecular Biology, Vol. 20, Protocols for Oligonucleotides and their Analogs, Synthesis and Properties*, Humana Press, Totowa, N.J., 143-164 (1993) each crude dimer-PEG 8 and 9 (130 mg) was separately treated with a solution (2 ml) of CH$_3$CN/EtOH (absolute)/ammonium hydroxide (45:45:10), vortexed and left at room temperature. After 30 min, ethylenediamine (2 ml) was added and the reaction was placed on a rotating mixer for 6 hours. The solution was diluted with 60 ml of water, neutralized with 6N HCl in 10% CH$_3$CN/H$_2$O (8.5 ml) and the solvents were evaporated under reduced pressure. The residue was suspended in a small amount of CHCl$_3$ (500 µl), sedimented, and the supernatant was analyzed by HPLC on silica gel with a gradient of 0-20% MeOH in CHCl$_3$ over 20 min at a flow rate of 5 ml/min. After purification on HPLC, compounds 10 and 11, obtained respectively from the deprotection of 8 and 9, were analyzed by $^{31}$P NMR. Assignment data: DMT-dAp(Me,Ax)dG 10: $^{31}$P NMR (CDCl$_3$): 32.60 ppm. Rt=8.20 min on HPLC; DMT-dAp(Me,Eq)dG 11: $^{31}$P NMR (CDCl$_3$): 32.40 ppm. Rt=7.40 min on HPLC.

Analogous to the procedure outlined in Preparation 4 through Example 2 for the synthesis of the monomer on the PEG support and the coupling to the stereospecific monomer to form the nucleotide with the stereospecific substituted phosphonate linkage, Preparation 6 begins the synthesis for attaching the 5'-protected monomer with the succinate linker, 5, to the solid support to form compound 12. The synthesis continues with the detritylation of 12 to form the 5'-deprotected monomer on a solid support 13 and the coupling (Example 3) to a stereospecific monomer 1 or 2, to form the nucleotide with the stereospecific substituted phosphonate linkage on a solid support, 14 and 15, respectively. Again, while the synthesis is shown for the sake of illustration with monomers 1 and 2, the procedure is equally applicable to any stereospecific 5'-protected nucleotide. Additionally, to couple additional stereospecific substituted monomers to the dimer, the procedure from Preparation 7 through Example 4 is repeated until the desired length is achieved. The complete synthesis is shown in Scheme 3 below.

Scheme 3
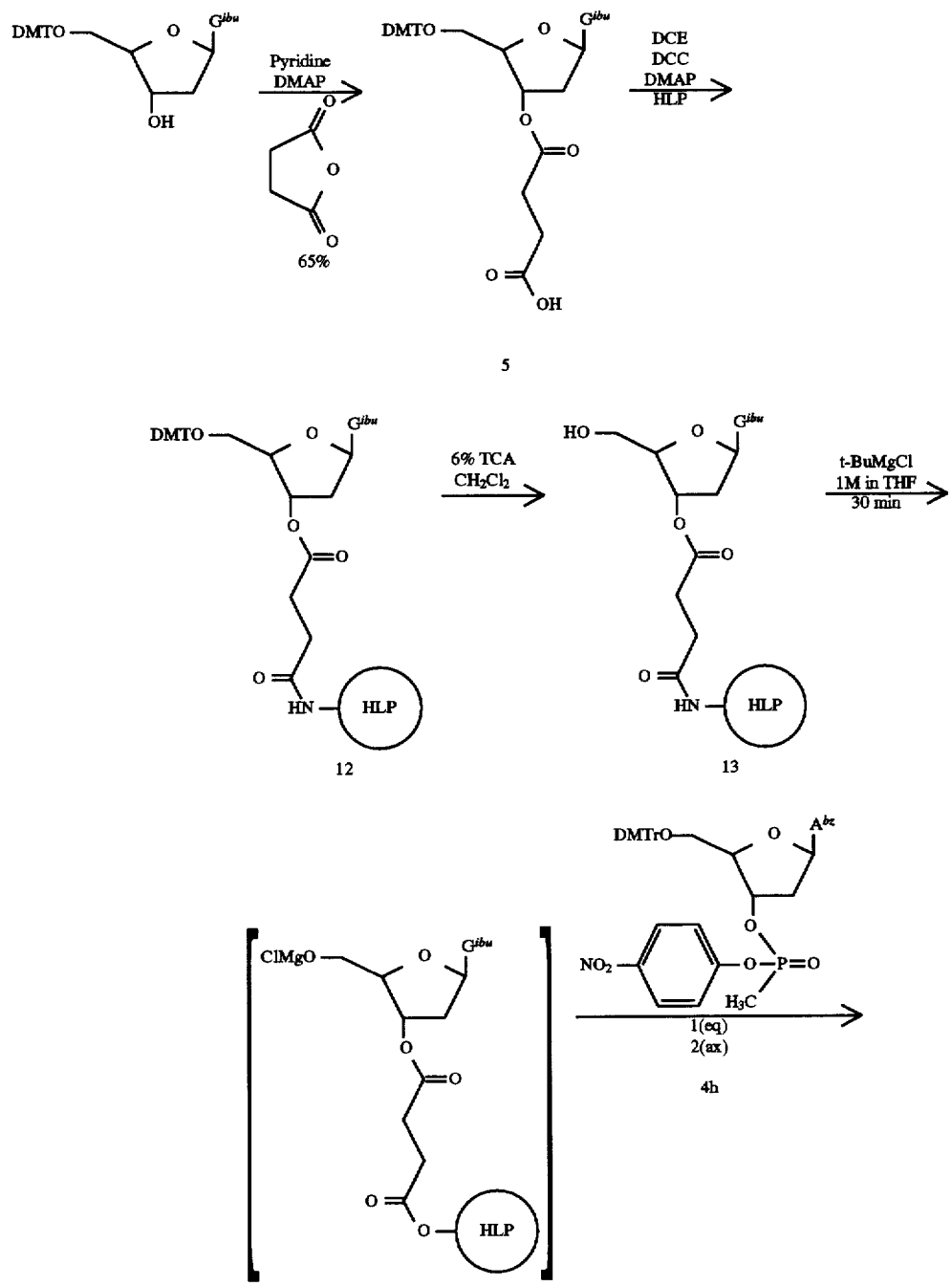

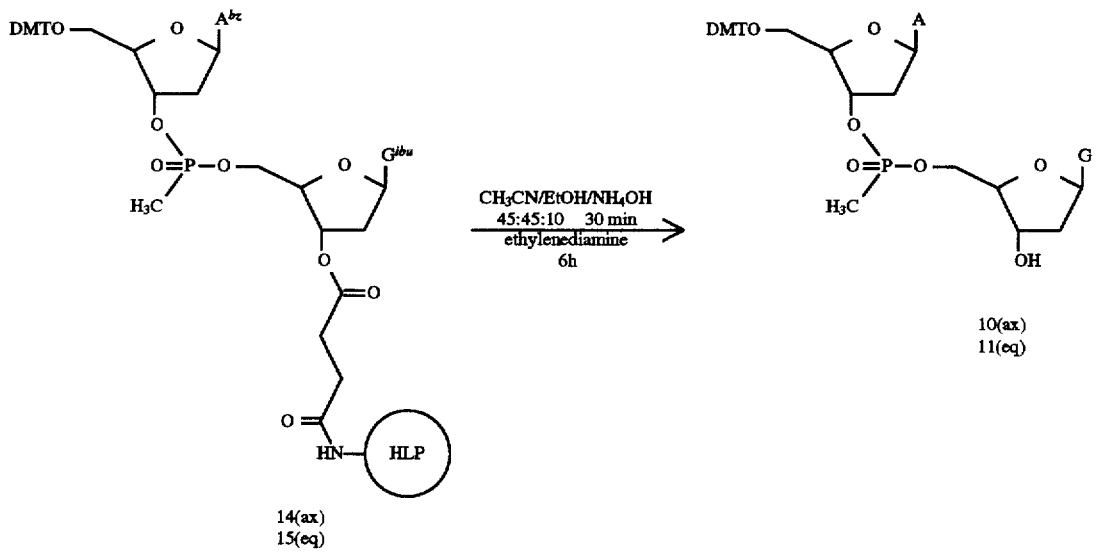

Preparation 6

5'-O-Dimethoxytrityl-N²-isobutyryl-3,-O-succinyl-2'-deoxyguanosine-HLP 12

High-loaded polystyrene beads derivatized with aminoethyl polyethylene glycol monomethylether (PEG$_{3000}$, approximately 1.25 g, 0.27 mmol of free NH$_2$-groups) were coevaporated 3 times with anhydrous pyridine (10 ml) and suspended in 12.5 ml of 1,2-dichloroethane (DCE) according to the method of Bonora et al., Nucleic Acids Res. 21: 1213–1217 (1993). The protected -3'-O-succinyl-2'-deoxyguanosine 5 (600 mg, 0.81 mmol) was dried by multiple coevaporation in anhydrous pyridine, then dissolved in 7 ml of DCE. Dicyclohexylcarbodiimide (100 mg, 0.45 mmol) was added under stirring at 0° C., and after 15 min. the precipitate of dicyclohexyl urea was removed by filtration. The filtrate was poured into the HLP suspension and dimethylaminopyridine (approximately 55 mg, 0.45 mmol) was added. The reaction mixture was concentrated to approximately 4 ml and left under stirring at room temperature for 20 hours. The solution was filtered, washed alternatively with Et$_2$O and absolute ethanol, and dried overnight under vacuum over KOH pellets. The complete elimination of unreacted 5 was confirmed by TLC (ethyl acetate/acetone/H$_2$O, 10:5:1). The yield of the reaction was determined by measuring the DMT absorption at 504 nm; the loading value of deoxyguanosine in compound 12 corresponds to approximately 140 µmol/g (approximately 1 g). The unreacted OH-groups of HLP were capped by treating with a solution containing 1 ml of 2,6-lutidine, 1 ml of N-methylimidazole and 1 ml acetic anhydride in 10 ml of CH$_3$CN. After 5 min at room temperature, compound 12 was filtered, washed alternatively with Et$_2$O and ethanol, and dried overnight under vacuum over KOH pellets (approximately 850 mg).

Preparation 7

N²-Isobutyryl-3'-O-succinyl-2'-deoxyguanosine-HLP 13:

Detritylation of the nucleoside was carried out by suspending compound 12 (approximately 700 mg, 98 µmol) in 7 ml of CH$_2$Cl$_2$ and adding dropwise 7 ml of a solution of 6% trichloroacetic acid in CH$_2$Cl$_2$ while stirring vigorously at 0° C. After 15 min, the polymer was filtered, washed three times with CH$_2$Cl$_2$, and dried over KOH pellets (approximately 650 mg). The complete elimination of the solution phase reagents would be confirmed by TLC (ethyl acetate/acetone/H$_2$O, 10:5:1).

EXAMPLE 3

5,-O-Dimethoxytrityl-N⁶-benzoyl-3'-O-methylphosphonate-2'-deoxyadenylyl-N²-isobutyryl-3'-O-succinyl-2'-deoxyguanosine-HLP (Ax) 14

Analogous to Example 1, Example 3 sets out a method of coupling the stereospecific monomer to the monomer with HLP support. To that end, compound 13 (loading 150 µmol/g, 200 mg, 30 µmol) was suspended in 500 µl anhydrous pyridine, to which a solution of tertbutylmagnesium chloride in dry THF (1M, 150 µl, 150 µmol) was added. After 30 min, Eq-isomer 1 (45 mg, 52 µmol) in anhydrous pyridine (200 µl) was added to the suspension of solid support. The reaction progress was monitored by TLC (ethyl acetate/acetone/H$_2$O, 10:5:1) and after 4 hours, TLC showed that Eq-isomer 1 (Rf 0.75) was converted into a new product (Rf 0). The reaction was quenched by washing of the solid support with an excess of Et$_2$O at 0° C. The yield of the coupling was evaluated by the DMT loading value of dimer 14, which corresponded to a quantitative yield (160 µmol/g, 200 mg) within the accuracy of the analytical method. The Ax stereo-specificity of the synthesis of 14 was assessed by HPLC, $^1$H and $^{31}$P NMR as distinguished from the crude deprotected products of solid support 10.

The Eq-dimer 15 is prepared according to the same methodology above utilizing the Ax-isomer 2.

EXAMPLE 4

5'-O-Dimethoxytrityl-3'-O-methylphosphonate-2'-deoxyadenylyl-3'-O-succinyl-2'-deoxyguanosine (Ax) 10

Example 4 is again comparable to the deprotection method set forth in Example 2, in which the crude dimer- HLP 14 (50 mg) was treated with a solution (2 ml) of CH₃CN/EtOH (abs)/ammonium hydroxide (45:45:10), vortexed and left at room temperature. After 30 min, ethylenediamine (2 ml) was added and the reaction was placed on a rotating mixer for 6 hours. The solution was diluted with 60 ml of water, neutralized with 6N HCl in 10% CH$_3$CN/H$_2$O (approximatively 8 ml) and the solvents were evaporated under reduced pressure. The beads were suspended in CHCl$_3$, filtered, rinsed with CHCl$_3$ (100 ml) and the solvents were evaporated under reduced pressure. The crude material was analyzed by HPLC on silica gel with a gradient of 0–20% MeOH in CHCl$_3$ over 20 min at a flow rate of 5 ml/min. The main peak eluting at 10.28 min was characterized by $^1$H NMR and $^{31}$P NMR; this peak corresponded to the Ax-dimer 10. Assignment data: DMT-dAp (Me, Ax) dG 10: Rf=0.62 (CHCl$_3$/MeOH, 90:10). Rt=10.28 min on HPLC. $^1$H NMR (CDCl$_3$): 1.48 (d, 3H, J$_{P-CH3}$=18 Hz, P—CH$_3$); 2.34 (t, 1H, H2'); 2.39 (m, 1H, H2"); 2.45 (m, 1H, H2'); 2.51 (m, 1H, H2"); 2.79 (m, 1H, H5'); 3.09 (dt, 1H, H5"); 3.22 (dd, 1H, H5'); 3.29 (dd, 1H, H5"); 3.75 (2s, 6H, OCH$_3$ of DMT); 4.16 (m, 1H, H4'); 4.23 (m, 1H, H4'); 5.28 (m, 1H, H3'); 5.42 (m, 1H, H3'); 6.08 (dd, 1H, H1'); 6.23 (t, 1H, H1'); 6.80–7.35 (m, 13H, aromatic protons of DMT); 7.44 (s, 1H, H8 of dG); 7.68 (s, 1H, H2 of dA); 7.83 (s, 1H, H8 of dA); 9.31 (broad, 1H, NH$_2$); 9.67 (broad, 1H, NH$_2$). $^{31}$P NMR (CDCl$_3$): 32.30 ppm.

Likewise, the Eq-dimer 11 is deprotected and cleaved from the HLP support by the procedure above from the Eq-dimer 15.

All references cited with respect to synthetic, preparative and analytical procedures are incorporated by reference.

The present invention may be embodied in other specific forms without departing from the spirit or essential attributes thereof and, accordingly, reference should be made to the appended claims, rather than to the foregoing specification, as indicating the scope of the invention.

What is claimed:

1. A method for producing a dinucleotide having a stereospecific substituted phosphonate linkage between a first and a second nucleoside, wherein said dinucleotide has the formula of A or A':

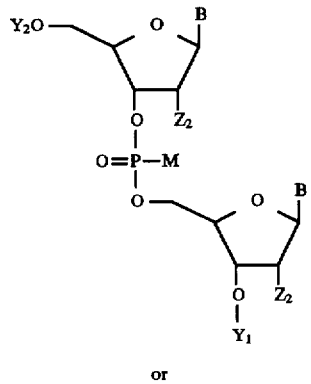

or

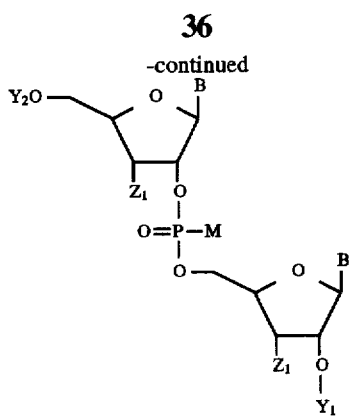

wherein:

Y$_1$ is a hydrogen or V$_1$;

Y$_2$ is a hydrogen or V$_2$;

B is independently selected from the group consisting of substituted and unsubstituted purine and pyridmidine bases;

Z$_1$ and Z$_2$ are independently selected from the group consisting of hydrogen, hydroxyl, and OY$_3$, where Y$_3$ is substituted or unsubstituted alkyl; and M is selected from the group consisting of alkyl, aryl, thio, borano and amino;

which method comprises:

(a) reacting a 5'-deprotected nucleoside having formula I or Ia:

wherein:

B$^a$ is selected from the group of substituted and unsubstituted protected purine and protected pyrimidine bases;

Z$_1$ and Z$_2$ are selected from the group consisting of hydrogen, hydroxyl and OY$_3$, where Y$_3$ is a substituted or unsubstituted alkyl; and V$_1$ is a solid support;

with a Grignard reagent of the formula, R—Mg—X, in at least a four fold molar excess with respect to the 5'-deprotected nucleoside, wherein:

R is a substituted or unsubstituted alkyl, allyl, aralkyl or aryl group; and

X is a halogen;

(b) coupling the product of (a) with a pure diastereoisomer of a 5'-protected nucleotide of formula II or IIa:

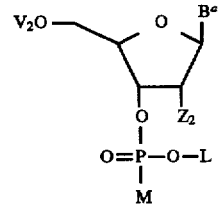

or

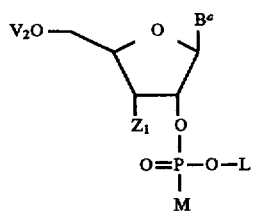

wherein:

37

$B^a$ is defined as above;
$V_2$ is a protecting group;
$Z_1$ and $Z_2$ are defined as above;
M is defined as above; and
L is a leaving group;
under anhydrous conditions sufficient to produce said stereospecific substituted phosphonate linkage; and
(c) when $V_2$ is a protecting group, optionally removing the $V_2$ protecting group.

2. A method for producing an oligonucleotide with a stereospecific substituted phosphorate linkages, wherein said oligonucleotide has the formula of Q or Q':

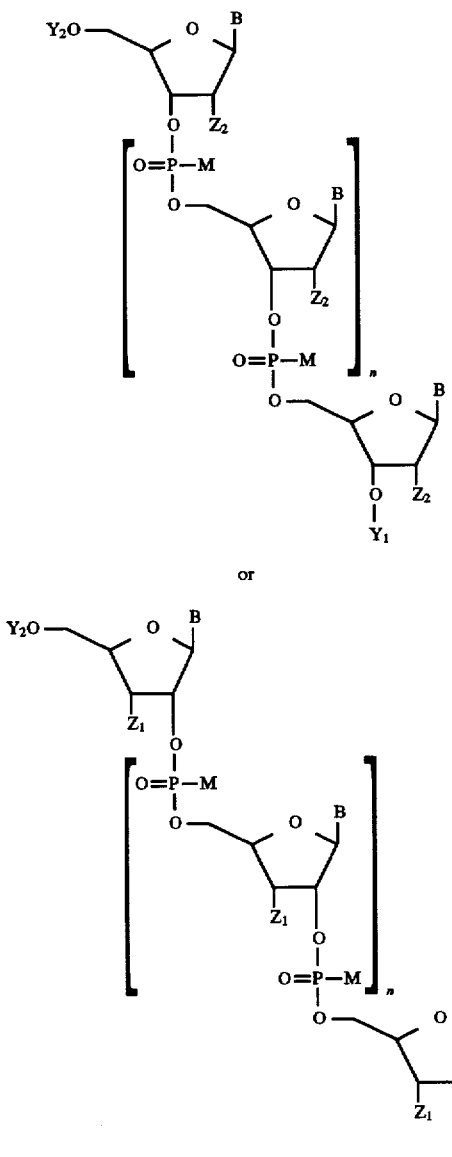

wherein:
$Y_1$ is a hydrogen or $V_1$;
$Y_2$ is a hydrogen or $V_2$;
B is independently selected from the group consisting of substituted and unsubstituted purine and pyridmidine bases;
$Z_1$ and $Z_2$ are independently selected from the group consisting of hydrogen, hydroxyl, and $OY_3$, where $Y_3$ is substituted or unsubstituted alkyl;

38

M is selected from the group consisting of alkyl, aryl, thio, borano and amino; and
n is an integer from 0 to 200;
which method comprises:
(a) reacting a 5'-deprotected nucleoside having formula I or Ia:

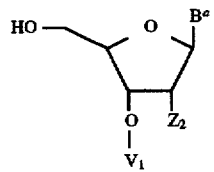

or

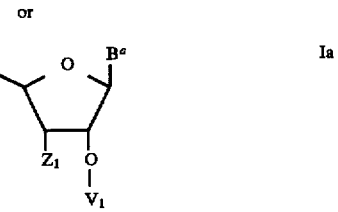

wherein:
$B^a$ is selected from the group of substituted and unsubstituted protected purine and protected pyrimidine bases;
$Z_1$ and $Z_2$ are selected from the group consisting of hydrogen, hydroxyl and $OY_3$, where $Y_3$ is a substituted or unsubstituted alkyl; and
$V_1$ is a solid support;
with a Grignard reagent of the formula, R—Mg—X, in at least a four fold molar excess with respect to the 5'-deprotected nucleoside, wherein:
R is a substituted or unsubstituted alkyl, allyl, aralkyl or aryl group; and
X is a halogen;
(b) coupling the product of (a) with a pure diastereoisomer of a 5'-protected nucleotide of formula II or IIa:

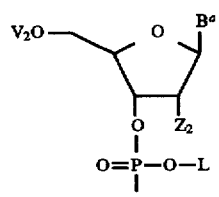

or

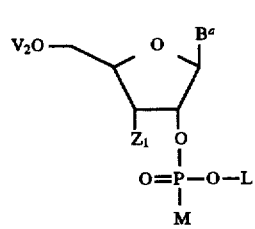

wherein:
$B^a$ is defined as above;
$V_2$ is a protecting group;
$Z_1$ and $Z_2$ are defined as above;
M is defined as above; and
L is a leaving group;
under anhydrous conditions sufficient to produce a new 5'-protected terminal nucleotide with said stereospecific substituted phosphonate linkage;

(c) removing the $V_2$ protecting group from said new 5'-protected terminal nucleotide;

(d) reacting the product of (c) with a Grignard reagent of the formula R—Mg—X, as defined above, in at least a four fold molar excess with respect to the 5'-deprotected nucleoside;

(e) reacting the product of (d) with another pure diastereoisomer of a 5'-protected nucleotide according to Formula II or IIa under conditions sufficient to produce a stereospecific substituted phosphonate linkage and so generate a new 5'-protected terminal nucleotide;

(f) repeating steps (c) through (e) to extend said polynucleotide chain n−1 times; and (g) what $V_2$ is a protecting group, optionally removing the $V_2$ protecting group.

3. A method for producing a dinucleotide having a stereospecific substituted phosphonate linkage between a first and a second nucleoside, wherein said dinucleotide has the formula of A or A':

wherein:

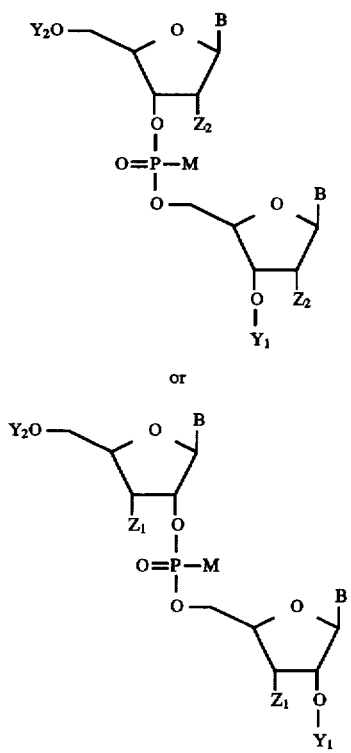

$Y_1$ is a hydrogen or $V_1$;

$Y_2$ is a hydrogen or $V_2$;

B is independently selected from the group consisting of substituted and unsubstituted purine and pyridmidine bases;

$Z_1$ and $Z_2$ are independently selected from the group consisting of hydrogen, hydroxyl, and $OY_3$, where $Y_3$ is substituted or unsubstituted alkyl; and M is selected from the group consisting of alkyl, aryl, thio, borano and amino;

which method comprises:

(a) reacting a 5'-deprotected nucleoside having formula I or Ia:

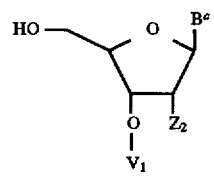

or

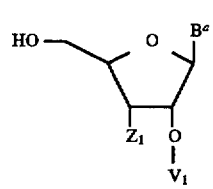

wherein:

$B^a$ is selected from the group of substituted and unsubstituted protected purine and protected pyrimidine bases;

$Z_1$ and $Z_2$ are selected from the group consisting of hydrogen, hydroxyl and $OY_3$, where $Y_3$ is a substituted or unsubstituted alkyl; and $V_1$ is a precipitable soluble polymer;

with a Grignard reagent of the formula, R—Mg—X, in at least a four fold molar excess with respect to the 5'-deprotected nucleoside, wherein:

R is a substituted or unsubstituted alkyl, allyl, aralkyl or aryl group; and

X is a halogen;

(b) coupling the product of (a) with a pure diastereoisomer of a 5'-protected nucleotide of formula II or IIa:

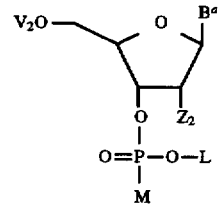

or

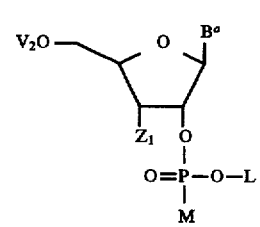

wherein:

$B^a$ is defined as above;

$V_2$ is a protecting group;

$Z_1$ and $Z_2$ are defined as above;

M is defined as above; and

L is a leaving group;

under anhydrous conditions sufficient to produce said stereospecific substituted phosphonate linkage;

(c) precipitating the product of (b) to remove the dinucleotide with said stereospecific substituted phosphonate/linkage from solution; and (d) when $V_2$ is a protecting group, optionally removing the $V_2$ protecting group.

4. A method for producing an oligonucleotide with a stereospecific substituted phosphonate linkages, wherein said oligonucleotide has the formula of Q or Q':

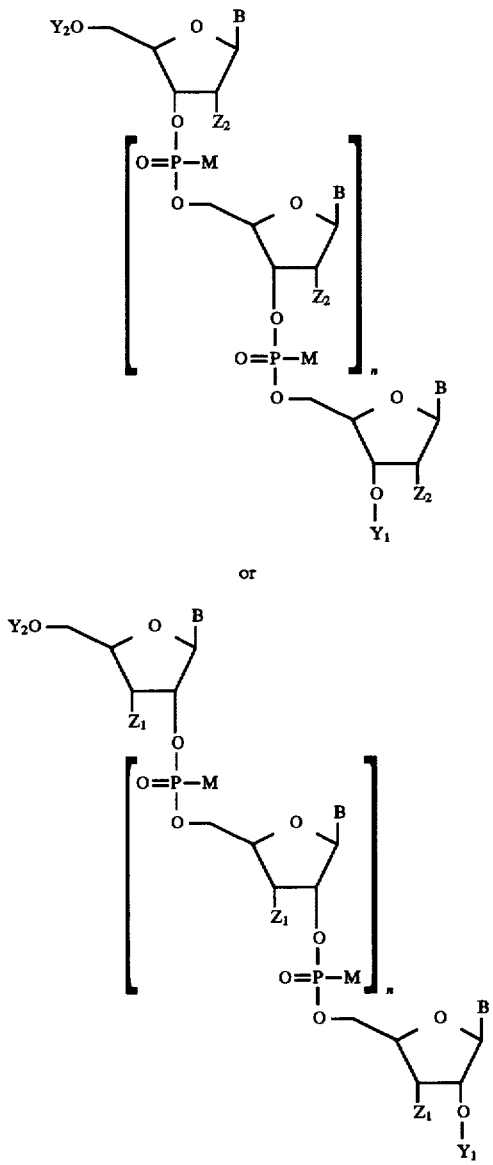

wherein:

$Y_1$ is a hydrogen or $V_1$;

$Y_2$ is a hydrogen or $V_2$;

B is independently selected from the group consisting of substituted and unsubstituted purine and pyridmidine bases;

$Z_1$ and $Z_2$ are independently selected from the group consisting of hydrogen, hydroxyl, and $OY_3$, whew $Y_3$ is substituted or unsubstituted alkyl;

M is selected from the group consisting of alkyl, aryl, thio, borano and amino; and n is an integer from 0 to 200;

which method comprises:

(a) reacting a 5'-deprotected nucleoside having formula I or Ia:

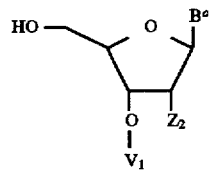

or

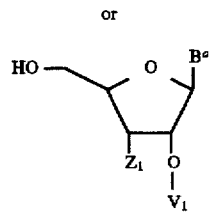

wherein:

$B^a$ is selected from the group of substituted and unsubstituted protected purine and protected pyrimidine bases;

$Z_1$ and $Z_2$ are selected from the group consisting of hydrogen, hydroxyl and $OY_3$, where $Y_3$ is a substituted or unsubstituted alkyl; and $V_1$ is a precipitable soluble polymer;

with a Grignard reagent of the formula, R—Mg—X, in at least a four fold molar excess with respect to the 5'-deprotected nucleoside, wherein:

R is a substituted or unsubstituted alkyl, allyl, aralkyl or aryl group; and

X is a halogen;

(b) coupling the product or (a) with a pure diastereoisomer of a 5'-protected nucleotide of formula II or IIa:

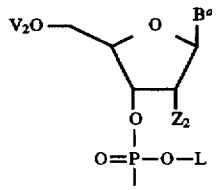

or

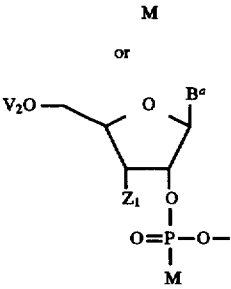

wherein:

$B^a$ is defined as above;

$V_2$ is a protecting group;

$Z_1$ and $Z_2$ are defined as above;

M is defined as above; and

L is a leaving group;

under anhydrous conditions sufficient to produce a new 5'-protected terminal nucleotide with said stereospecific substituted phosphonate linkage;

(c) precipitating the product of (b) to remove the oligonucleotide with said stereospecific substituted phosphonate linkage from solution;

(d) dissolving the product of (c) in a solvent to return the product to solution to add another nucleotide with said stereospecific phosphorate linkage to said oligonucleotide formed in step (b);

(e) removing the $V_2$ protecting group from the new 5'-protected terminal nucleotide;

(f) reacting the product of (e) with a Grignard reagent of the formula R—Mg—X, in at least a four fold molar excess with respect to the 5'-deprotected nucleoside, defined as above;

(g) reacting the product of (f) with another pure diastereoisomer of a 5'-protected nucleotide according to Formula II or IIa under conditions sufficient to produce a stereospecific substituted phosphonate linkage and so generate a new 5'-protected terminal nucleotide;

(h) repeating steps (b) through (g) to extend said polynucleotide chain n−1 times; and (i) when $V_2$ is a protecting group, optionally removing the $V_2$ protecting group.

5. A method for producing a Grignard-nucleoside intermediate on a support, which intermediate is of the formula III or IIIa:

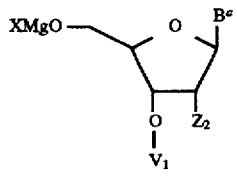

or

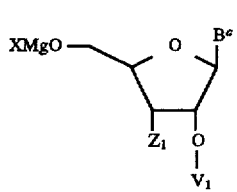

wherein:

$B^a$ is selected from the group consisting of substituted and unsubstituted protected purine and protected pyrimidine bases;

$Z_1$ and $Z_2$ are selected from the group consisting of hydrogen, hydroxyl and $OY_3$, where $Y_3$ is a substituted or unsubstituted alkyl;

X is a halogen; and $V_1$ is selected from the group of a solid support and a precipitable soluble polymer;

which method comprises:

reacting a 5'-deprotected nucleoside having formula I or Ia:

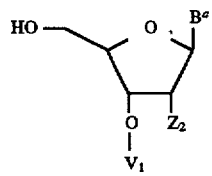

or

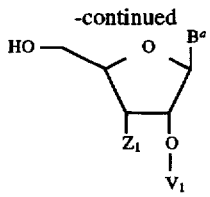

wherein:

$B^a$ is defined as above;

$Z_1$ and $Z_2$ are defined as above; and $V_1$ is defined as above;

with a Grignard reagent of the formula, R—Mg—X, in at least a four fold molar excess with respect to the 5'-deprotected nucleoside, wherein:

R is a substituted or unsubstituted alkyl, allyl, aralkyl, or aryl group; and

X is defined as above;

under anhydrous conditions sufficient to produce said Grignard-nucleoside intermediate.

6. The method of claim 2 or 4 wherein n is at least 3.

7. The method of claim 1 or 2 wherein the solid support is polystyrene or a polyethylene glycol coated polystyrene.

8. The method of claim 3 or 4 wherein the precipitable soluble polymer is polyethylene glycol.

9. The method of claim 3 or 4 wherein the precipitable soluble polymer is polyethylene glycol with a molecular weight from about 4,000 g/mole to about 12,000 g/mole.

10. The method of any one of claims 1–4 wherein M is lower alkyl, lower aryl, lower thioalkyl, $BH_3$, $BF_3$, lower boranoalkyl, and lower aminoalkyl.

11. The method of claim 10 wherein M is methyl.

12. The method of claim 2 or 4 wherein said anhydrous conditions sufficient to produce said stereospecific substituted phosphonate linkage comprise a time, a temperature, a solvent or a reactant concentration sufficient for nucleophilic attack by the 5'-oxygen of said first nucleoside or said 5'-terminal nucleoside upon the phosphorus of the stereospecific substituted phosphonate nucleotide to displace the leaving group and invert the phosphorus configuration.

13. The method of claim 12 wherein said time is about 1 hour to about 10 hours.

14. The method of claim 12 wherein said time is about 1 hour to about 5 hours.

15. The method of claim 5 wherein the Grignard reagent is tert-butylmagnesium chloride.

16. A method for producing a dinucleotide having a stereospecific substituted phosphonate linkage between a first and a second nucleoside, which method comprises:

(a) reacting a 5'-deprotected base protected nucleoside linked to a solid support through the 2' or 3' position of said nucleoside, with a compound of the formula R—Mg—X, in at least a four fold molar excess with respect to the 5'-deprotected nucleoside, where R is a substituted or unsubstituted alkyl, allyl, aralkyl or aryl, and X is a halogen;

(b) coupling the product of (a) with a stereospecific base protected nucleotide, having a substituted phosphoryl moiety of the formula

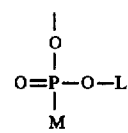

linked through the 2' or 3' position of said nucleotide, where M is selected from the group consisting of alkyl, aryl, thio, borano and amino, and L is a leaving group under anhydrous conditions sufficient to link the base protected nucleoside of (a) to the substituted phosphoryl moiety of said nucleotide arid generate said stereospecific phosphonate linkage in a new 5'-terminal nucleotide;

(c) optionally removing the protecting group from the new 5'-terminal nucleotide.

17. A method of producing an oligonucleotide having stereospecific substituted phosphonate linkages, which method comprises:

(a) reacting a base protected nucleoside linked to a solid support through the 2' or 3' position of said nucleoside, with a compound of the formula R—Mg—X, in at least a four fold molar excess with respect to the 5'-deprotected nucleoside, where R is a substituted or unsubstituted alkyl, allyl, aralkyl or aryl, and X is a halogen;

(b) coupling the product of (a) with a stereospecific base protected nucleotide, having a substituted phosphoryl moiety of the formula

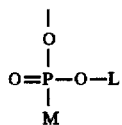

linked through the 2' or 3' position of said nucleotide, where M is selected from the group consisting of alkyl, aryl, thio, borano and amino, and L is a leaving group, under anhydrous conditions sufficient to link the base protected nucleoside of (a) to the substituted phosphoryl moiety of said nucleotide and generate said stereospecific phosphonate linkage in a new 5'-terminal nucleotide;

(c) removing the protecting group from the new 5'-terminal nucleotide;

(d) reacting the product of (c) with a compound of the formula R—Mg—X, in at least a four molar excess with respect to the 5'-deprotected nucleoside, defined as above; and (e) repeating steps (b) through (d) one or more times to extend said polynucleotide to the desired length.

18. A method for producing a dinucleotide having a stereospecific substituted phosphonate linkage between a first and a second nucleoside, which method comprises:

(a) reacting a base protected nucleoside linked to a precipitable soluble polymer through the 2' or 3' position of said nucleoside, with a compound of the formula R—Mg—X, in at least a four fold molar excess with respect to the 5'-deprotected nucleoside, where R is a substituted or unsubstituted alkyl, ally, aralkyl or aryl, and X is a halogen;

(b) coupling the product of (a) with a stereospecific base protected nucleotide, having a substituted phosphoryl moiety of the formula

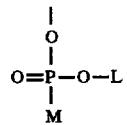

linked through the 2' or 3' position of said nucleotide, where M is selected from the group consisting of alkyl, aryl, thio, borano and amino, and L is a leaving group under anhydrous conditions sufficient to link the base protected nucleoside of (a) to the substituted phosphoryl moiety of said nucleotide and generate said stereospecific phosphonate linkage in a new 5'-terminal nucleotide;

(c) precipitating out the product of (13) from solution to remove said dinucleotide having a stereospecific substituted phosphonate linkage; and (d) optionally removing the protecting group from rig new 5'-terminal nucleotide.

19. A method of producing an oligonucleotide having stereospecific substituted phosphorate linkages, which method comprises:

(a) reacting a base protected nucleoside linked to a precipitable soluble polymer through the 2' or 3' position of said nucleoside, with a compound of the formula R—Mg—X, in at least a four fold molar excess with respect to the 5'-deprotected nucleoside, where R is a substituted or unsubstituted alkyl, allyl, arylalkyl or aryl, and X is a halogen;

(b) coupling the product of (a) with a stereospecific base protected nucleotide, having a substituted phosphoryl moiety of the formula

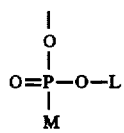

linked through the 2' or 3' position of said nucleotide, where M is selected from the group consisting of alkyl, aryl, thio, borano and amino, and L is a leaving group, under anhydrous conditions sufficient to link the base protected nucleoside of (a) to the substituted phosphoryl moiety of said nucleotide and generate said stereospecific phosphonate linkage in a new 5'-terminal nucleotide;

(c) precipitating out the product of (b) from solution to remove said dinucleotide having a stereospecific substituted phosphonate linkage;

(d) dissolving the product of (c) in a solvent to return the product to solution to generate a new oligonucleotide with said stereospecific substituted phosphonate linkage;

(e) removing the protecting group from the new 5'-terminal nucleotide;

(f) reacting the product of (e) with a compound of the formula R—Mg—X, as defined above, in at least a four fold molar excess with respect to the 5'-deprotected nucleoside;

(g) reacting the product of (f) with another stereospecific base protected nucleotide of the formula of (b) under anhydrous conditions sufficient to generate a new stereospecific phosphonate linkage in a new 5'-terminal nucleotide;

(h) repeating steps (b) through (g) one or more times to extend said oligonucleotide to the desired length; and (i) optionally removing the protecting group from the new 5'-terminal nucleotide.

* * * * *